United States Patent [19]

Ajani et al.

[11] Patent Number: 4,988,724
[45] Date of Patent: Jan. 29, 1991

[54] METHODS AND IMPROVED FORMULATIONS FOR THE DETERMINATION AND TREATMENT OF MALIGNANT DISEASE IN PATIENTS

[75] Inventors: Jaffer Ajani; Bruce Grossie, Jr.; Kenji Nishioka; David M. Ota, all of Houston, Tex.

[73] Assignee: Board of Regents, The University of Texas System, Austin, Tex.

[21] Appl. No.: 282,126

[22] Filed: Dec. 9, 1988

[51] Int. Cl.$^5$ .................... A61K 31/41; A61K 31/40; A61K 31/195
[52] U.S. Cl. .................... 514/399; 514/412; 514/428; 514/561; 514/562; 514/566; 514/568
[58] Field of Search ............... 514/412, 428, 561, 562, 514/566, 568, 399

[56] References Cited

U.S. PATENT DOCUMENTS 3,832,465  8/1974  Ghadimi .
3,950,529  4/1976  Fischer et al. .

OTHER PUBLICATIONS

Nishioka et al., (1988), Int. J. Cancer, 42: 744–747.
Byus et al., (1987), Proceedings of AACR, 28: 158 (#630).
Garewal et al. (1988), Cancer Research, 48: 3288–3291.
Majumdar et al., (1987), Life Sciences, 41: 961–966.
Malo et al., (1987), Experientia, 44: 251–252.
Morris, J. (1985), J. Nutr. 115: 524–531.
Seidel et al., (1985), Am. J. Physiol, 249: G434–G438.
Luk et al., (1984), J. Clin. Invest., 74: 698–704.
Lundell et al., (1986), Scand. J. Gastroenterology, 21 (7):829–832.
J. L. Rombeau & M. D. Caldwell (eds.), in Parenteral Nutrition, 2: 100–134, (1986).
Braun Amino Acid Suppliers, Combiplasmal® S-3,5, Aminoplasmal Paed.
Salvia Amino Acid Suppliers, Aminomel® 10X-E Saliva.
Phimmer Amino Acid Suppliers, Comafusion® Llepar.
Grossie et al. (1986), Cancer Research, 46:3464–3468.
Ota et al., (1986), Int. J. Cancer, 38:245–249.
Poedikayal et al., J. Nutrition, 116 (4), pp. 545–551, 1986, Biological Abstracts, vol. 82, 1986, Abstract 26473.

Primary Examiner—Mukund J. Shah
Assistant Examiner—E. C. Ward
Attorney, Agent, or Firm—Arnold, White & Durkee

[57] ABSTRACT

Disclosed are total parenteral nutrition formulations which include essential amino acids in combination with either arginine or ornithine, for use in the detection of recurrent malignant disease in patients. Such formulations stimulate tumor-specific polyamine production to a greater extent than non-tumor related polyamine production. Additionally, such formulations were found to specifically promote an increase in red blood cell putrescine levels of tumor-bearing rats. Nontumor-bearing rats were not found to be similarly reactive to these formulations. Methods for making and administering these formulations as well as their use in preventing DFMO-induced toxicity are also disclosed.

Also disclosed are parenteral nutritional formulations which include both citrulline and ornithine which have an arginine concentration of less than about 0.10% by weight final concentration. These formulations inhibit tumor growth and are particularly suited to provide nutritional support for patients with malignant disease. These formulations act to modify the tumor cells ability to compete with normal host tissue for nutrients by modifying the specific content of amino acids administered to the patient. The exact mechanism by which such a formulation alters tumor metabolism is not known, but it has been shown that some of the described formulations result in a reduced rate of tumor cell growth when compared to standard arginine-containing TPN solutions. A method for inhibiting tumor growth and a process for preparing the tumor-inhibiting formulation are also described.

19 Claims, 5 Drawing Sheets

METHODS AND IMPROVED FORMULATIONS FOR THE DETERMINATION AND TREATMENT OF MALIGNANT DISEASE IN PATIENTS

BACKGROUND OF THE INVENTION

Reference is made to Applicant's co-pending applications, Ser. Nos. 820,517, filed Jan. 17, 1986 and 002,890, filed Jan. 13, 1987. The government may own certain rights in the present invention pursuant to NCI grant ROI CA3 4-465.

1. FIELD OF THE INVENTION

The present invention relates to improved formulations and methods for the detection of malignant disease in a patient. More particularly, the present invention is directed to formulations which augment tumor related increases in a patient's polyamine level and which additionally prevent drug related side effects in patients undergoing ornithine decarboxylase inhibitor therapy.

The present invention is also directed to formulations which reduce tumor growth rate in a patient.

2. DESCRIPTION OF THE RELEVANT ART

Polyamines are important in the regulation of protein, RNA and DNA synthesis in mammalian systems and are essential for cell proliferation. The increased excretion of polyamines in the urine of patients with cancer was reported by Russell, D.H. (1971), *Nature*, 233: 144-145. Based on animal studies of tumor growth and regression, spontaneously and in response to radiation and chemotherapy, a model was proposed by Russell, et al. (1975), *Lancet*, 2: 797-799, to summarize the potential role of polyamines as biochemical markers of human tumor cell growth and death. Such observations raise the possibility that measurement of polyamine levels in clinical fluids and tissue specimens could be useful in the diagnosis and elevation of patients with cancer. For our review of the diagnostic role of polyamines in cancer, see "Polyamines and the Clinical Elevation of Patients with Cancer", Chapter 10, in *Progress in Cancer Research and Therapy*, Raven Press, New York, 1978.

Although polyamine measurements in the urine, plasma and whole blood of patients initially held promise as tumor markers, their use for detecting recurrent systemic disease has been limited. This unreliability is due to below clinical sensitivity (high number of false negatives) and specificity (high number of false positives). Despite numerous reports of elevated polyamines in patients with malignant disease, overlapping standard deviations of polyamine levels between cancer and non-cancer patients reduce their sensitivity to accurately detect malignant disease at an early stage. Furthermore, increased polyamine levels have been associated with nonmalignant disease states such as certain inflammatory and infectious diseases. Such unreliability could be removed by the availability of techniques for specifically increasing polyamine levels observed in false positives such as infectious disease patients. Accordingly, techniques for improving the sensitivity and specificity of the polyamine level test as an indicator of malignant disease in man would represent a significant advance in medical science.

Nutritional status plays an important role in the clinical management of patients with malignant disease. Warren, S. (1932) *Am. J. Med. Sci.:* 184: 610, and, more recently, others (DeWys, W.D., Begg. C., Lavin, P.T., et al. (1980) *Am. J. Med Sci.:* 69: 491–497) have shown that malnutrition can significantly influence the mortality and shorten the survival time of patients with disseminated disease. Furthermore, cancer therapy may be delayed in patients with a compromised nutritional status for fear of reducing oral intake. In 1967, Dudrick, et al. (1968) *Surgery*, 64: (1969) 134, *Ann. Surg.*, 69: 974 introduced a safe and effective method to parenterally feed patients until gastrointestinal function could be restored. Soon, total parenteral nutrition (TPN) was used for patients in many diseased states such as congenital anomalies of the gastrointestinal tract, trauma, inflammatory bowel disease, and liver disease. Fischer, U.S. Pat. No. 3,950,529 (1976).

Copeland and Dudrick, (1976) Curr. Probl. Cancer, 1: 3, recognized the potential of parenteral feeding techniques to solve nutritional problems in a cancer population. It was then theorized that if nutritional therapy in conjunction with cancer therapy could improve host nutritional status, then host survival should improve. Also, preliminary uncontrolled studies showed that host tolerance and tumor response to antineoplastic therapy improved when malnourished patients received TPN, advancing the theory that force feeding of nutrients reduced host toxicity and sensitized tumors to chemotherapeutic agents (Isell, B.F., Valdivieso, M., Zaren, H.A., et al. (1978) *Cancer Treat Rep.*, 62: 1139; Lanzotti, V.J., Copeland, E.M. III, George, S.L., et al. (1975) *Cancer Treat Rep.*, 59: 437).

In the 1970's, several prospective randomized trials were conducted to test these theories. These trials involved patients requiring systemic chemotherapy for testicular carcinoma, small cell lung carcinoma, lymphoma, lung adeno carcinoma and colorectal carcinoma (Lanzotti, et al., (1975) *Cancer Treat. Rep.*, 59: 437; Samuels, M.L., et al. (1981) *Cancer Treat, Rep.*, 65: 615-627; popp, M.D., et al., (1981) *Cancer Treat. Rep.* 65: 129-135; Valdivieso, M., et al., (1981) *Cancer Treat Rep.*, 659 (suppl. 5): 145; Nixon, D.W., et al., (1981) *Cancer Treat. Rep.*, 65 (suppl. 5): 121-128; Jordan, W.M., et al., (1987) *Cancer Treat. Rep.*, 65: 197. The results of these trials showed that TPN did not improve host tolerance to chemotherapy. Furthermore, tumor response rates were independent of host nutritional status. In fact, one report suggests that TPN may have led to earlier patient demise secondary to progressive disease. Nixon, D.W., et al., (1981), *Cancer Treat. Rep.*, 65 (suppl. 5): 121-128).

Several early studies in animal-tumor models in the late 1970's and early in 1980 showed that nutritional therapy (TPN) can result in tumor growth and, in some cases, accelerate growth. Cameron, I.L., (1981), Cancer Treat. Rep., 65 (suppl. 5): 93; Buzby, G.P., Mullen, J.L., Stein, T.P., et al., (1980), Cancer 45: 2940. For some tumors, tumor growth can also occur during host starvation, emphasizing that tumors will obtain their exogenous or endogenous nutrients for their energy needs and biosynthetic pathways, to the host's demise. (Sauer, L.A., Nagel, W.O. Dauchy, R.T., et al., (1986) *Cancer Res.*, 46: 3469). Therefore, the use of a standard TPN formulation was contraindicated for patients with malignant disease.

These preliminary studies, however, did not consider significant biological aspects of host-tumor metabolism, namely the competition of host and tumor tissues for nutrients in devising an appropriate TPN regiment. Accordingly, a formulation which would provide nutritional support to the patient with malignant disease without stimulating tumor growth would significantly advance the currently practiced clinical oncological management of these patients.

SUMMARY OF THE INVENTION

It is an object of the present invention to provide an amino acid formulation for improving the diagnostic reliability of polyamine level determinations as indicators of malignant disease in man. In particular, amino acid formulations prepared in accordance with the present invention and administered to patients promote a specific elevation in the polyamine level of patients with primary or recurrent malignant disease. The term amino acid, as used herein, is defined to include all amino acid-derived compounds which will effectively provide the free l-amino acid at the intracellular level. For example, peptides are amino acid-derived compounds that when acted upon by metabolic enzymes will provide the free amino acid. Similarly, amino acid derivatives, for example, n-acetylated amino acids, are included within the meaning of the term amino acid.

Formulations include a pharmacologically acceptable amount of a polyamine precursor in combination with at least one of the amino acids, preferably one of the essential amino acids. Essential amino acids as used herein refer to those found by William Rose and his associates to be essential in that they are not normally metabolically produced by the body. For example, see Rose (1949) *Fed. Proc.*, 8:546 and Rose et al. (1955) *J. Biol. Chem.*, 217:987. Additionally, as used herein, polyamine precursors are defined as those amino acids in the metabolic pathway of urea and polyamine production and include methionine, arginine, ornithine and citrulline.

Such formulations may include any non-toxic amount of each of the included amino acids. Therefore, for the purposes of the present invention, a pharmacologically acceptable amount of an included amino acid generally means any level of that amino acid which is at least high enough to supply minimal metabolically sufficient concentrations of that amino acid to the target cells. However, such formulations could presumably incorporate amino acid concentrations which approach toxicity-inducing levels, for example, in an attempt to "tailor" formulations to fit a particular patient population. In a preferred embodiment, the concentration of included amino acids found to promote good polyamine responses exhibited a range from 50 to 200 mg. for tryptophan to 250 to 1400 milligrams for leucine in every 100 milliliters of a parenteral formulation. The preferred range for arginine, ornithine or methionine, the polyamine precursors, is between 50 and 750 mg/100 ml. of solution, however, higher concentrations may be employed where desired. In a more preferred embodiment, the concentration of polyamine precursor is approximately 30 mM (which, for example, corresponds to 450 mg. ornithine/100 ml. of the formulation).

In another embodiment, the amino acid formulation is conveniently supplied by combining pharmacologically acceptable amounts of ornithine or arginine with commercially available parenteral feeding solutions. Such feeder solutions could prove useful both as parenteral solutions tailored to maximize the sensitivity of detection of recurrent malignant disease and as adjuvants to the cancer-screening of patients who are undergoing parenteral feeding.

It is a further object of the present invention to provide methods for detecting cancer in a patient which generally includes administering to the patient one of the parenteral amino acid formulations described and detecting an increase in the patient's polyamine level following administration of the formulation, a relative increase being indicative of cancer in the patient. Relative increase in polyamine levels is meant to include either relative increases with respect to the cancer patient's own pre-administration level or with respect to "normal" patient population's average pre- or post administration polyamine levels.

Although the full advantages of the present invention are particularly exemplified through detection of a relative increase in putrescine, measurement of all of the polyamines, including spermidine, spermine and putrescine, is sufficient for most uses.

Similarly, although polyamine levels may be determined in any of a number of patient samples, including cerebrospinal fluid, urine, plasma, serum and whole blood, in a preferred embodiment, the patient's red blood cell (RBC) polyamine levels are measured as a more sensitive indicator of polyamine levels.

It is still further object of the present invention to provide formulations for use in preventing or reducing the occurrence of ODC-related toxicities in patients undergoing ODC therapy. In this regard, it is demonstrated herein that amino acid formulations which are formulated to include a polyamine precursor, preferably ornithine, can reduce or reverse DFMO induced thrombocytopenia. Moreover, it has been found that for such uses, polyamine precursors may be administered either alone or in combination with other amino acids.

It is still a further feature of the present invention to provide formulations that reduce tumor growth rate in patients with malignant disease. In this regard, it is demonstrated herein that amino acid formulations which are formulated to decrease or eliminate arginine and which include ornithine can reduce the rate of TPN induced tumor growth. It is further proposed that a formulation which includes citrulline can be used in conjunction with or instead of ornithine to furnish necessary urea cycle substrates. In one preferred embodiment, the final concentration of included arginine is less than about 0.10% by weight where citrulline is present in a non-toxic pharmacologically acceptable concentration. A preferred embodiment of this particular formulation includes citrulline in about a range of 0.01 to 2% by weight final concentration. In another preferred embodiment, the concentration of included arginine was less than about 0.05% by weight of the formulation where ornithine and citrulline are present in a non-toxic pharmacologically acceptable concentration. A preferred embodiment of this particular formulation includes ornithine in a greater than 0.5% by weight final concentration and citrulline in a range of 0.01 to 2% by weight final concentration of the formulation.

Another embodiment of the formula does not include citrulline, but does include arginine in a less than about 0.10% by weight final concentration and ornithine in a non-toxic pharmacologically acceptable concentration. A preferred embodiment of this particular formulation includes ornithine in about a 1% by weight final concentration. However, it is postulated that the lower the concentration of arginine in each of the above formulations, the greater the tumor-inhibiting effect will be.

In an additional embodiment, the formulation further includes a mixture of essential amino acids and at least one non-essential amino acid. The non-essential amino acid of choice in one such preferred embodiment is alanine, to be included in any non-toxic, pharmacologically acceptable concentration. One particular embodiment of the present invention includes alanine in about a 1% by weight final concentration. These particular preferred embodiments are arginine-free. Such formulations may include any non-toxic, pharmacologically acceptable concentration of each of the included essential amino acids.

An additional preferred embodiment of the formulation includes a mixture of essential amino acids in pharmacologically acceptable concentrations, less than about 0.10% arginine by weight final concentration, both ornithine and citrulline at a non-toxic, pharmacologically acceptable concentration, and a mixture of the non-essential amino acids: alanine (200-3500 mg./100 ml); glycine (250-3000 mg./100 ml); proline (100-1500 mg./100 ml) and serine (5-650 mg./100 ml). A pharmacologically acceptable amount of an included amino acid in any of the above formulations generally means any level of that amino acid which is at least high enough to supply minimal metabolically sufficient concentrations of that amino acid to the target in the feeding solution cells, but not so high as to be toxic. For example, concentrations in the range of about 0.01% and 5.0% are for most amino acids considered non-toxic and pharmacologically acceptable. This range applies as well to citrulline and ornithine. Also, it is observed that the lower the concentration of arginine in each of the above formulations, the greater the tumor-inhibiting effect will be. In fact, a less than about 0.10% by weight final weight concentration of arginine is hypothesized to have a greater tumor growth inhibiting effect. A formulation without arginine would provide the most superior tumor growth inhibiting effect of all the presently disclosed formulations.

It is a further object of the present invention to provide methods for inhibiting or eliminating tumor growth in a patient with malignant disease, which generally includes administering to the patient one of the amino acid formulations described herein. The mode of administering said formulation is parenterally, however the formulas could be modified so as to allow oral administration. Successful inhibition of tumor growth may be detected through demonstration of relatively increased survival rates of formulation-receiving patients compared to standard TPN receiving patients. Survival data taken from patients undergoing chemotherapy and cancer patients being prepared for surgery suggest that standard TPN support solutions may actually decrease survival rate. However, nutritional support is often times indicated in persons undergoing chemotherapy, as intestinal complications accompanying such treatment make oral feeding difficult. Patients with acute disruption of gastrointestinal functions and those with such disorders awaiting major surgery frequently suffer from a compromised nutritional status. Correction of varying states of malnutrition with a tailored amino acid regimen is hypothesized to constitute both a life-sustaining tactic until intestinal function returns to normal and a beneficial pre-operative practice. A decrease in postoperative complications with shorter recovery times are particular expected benefits of such a pre-operative practice. The relative nutritional status of a patient may be determined by numerous methods well know to those of skill in the art, including measurement of plasma proteins, anthropometric measurements, immunological testing, urine chemistries and body compositional studies.

An additional object of the present invention is to provide a process for preparing a formulation that decreases tumor growth rate. In its broadest embodiment, this process comprises the steps of combining non-toxic, pharmacologically acceptable amounts of citrulline with arginine, and adding to this combination a sufficient volume of appropriate liquid medium so as to achieve about a pharmacologically acceptable concentration of citrulline and a less than 0.10% by weight concentration of arginine. In a preferred embodiment, a glucose solution or filtered water is an appropriate liquid medium. It has been found that for such uses, this solution may be administered in combination with other amino acids and ornithine.

BRIEF DESCRIPTION OF THE DRAWINGS

Table I. A listing of several parental formulations and their manufacturers which include the indicated amount of amino acids per each 100 ml of the formulation.

This study suggests that arginine may be important in stimulating tumor growth. Bars indicate standard deviation. Numbers indicate number of animals. a=$P<0.05$ vs CONTROL; b=$P<0.05$ vs TPN; c=$P<0.05$ vs EAA.

Figure 8:
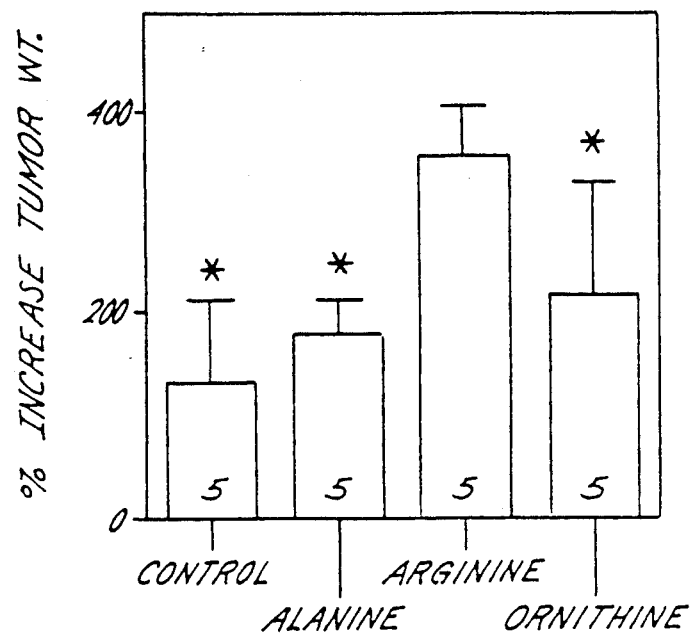

FIG. 8. Graph demonstrates the role of polyamine precursors in TPN-induced tumor growth observed in Example IX. Approximately 4g. Ward colon carcinomas were established in Fisher 344 rats that received parenteral therapy. Rats were then randomized to four treatment groups CONTROL (i.v. saline+chow), ALANINE, [(500 ml D50 +250 ml. 5.2% EAA+alanine (3.3 mmol/100 ml)], ARGININE [(500 ml D50+250 ml. 5.2% EAA+arginine (3.3 mmol/100ml), and ORNITHINE [(500 ml D50+250 ml. 5.2% EAA +ornithine. (See Table IX). The regimens were administered by continuous i.v. infusion for 6 days. The results show the percent increase in tumor weight during the 6-day infusion with the bars indicating the standard deviation. The numbers indicate number of rats. * indicates $P<0.05$ compared with the ARGININE group. CONTROL and ORNITHINE were not significantly different. The data indicate that the arginine in TPN solutions may stimulate tumor growth while ornithine does not.

Figure 9:
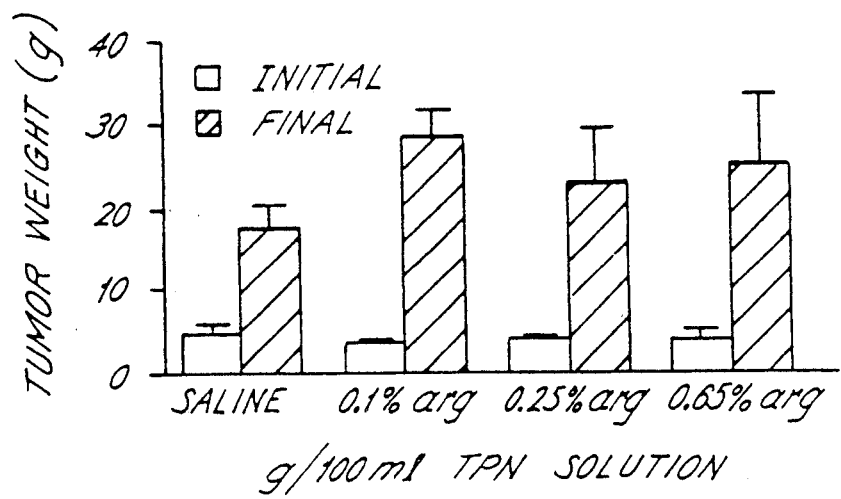

FIG. 9. Graph demonstrates the effect of decreasing arginine concentrations on tumor growth measured in grams. As shown, arginine concentrations as low as 0.1% arginine in the TPN solution may increase tumor growth.

Figure 10:
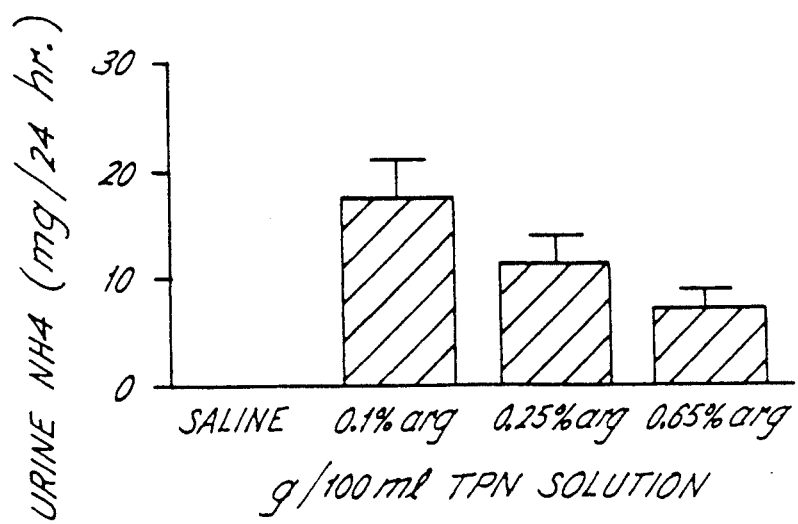

FIG. 10. Graph demonstrates the effect of decreasing arginine concentrations on urine ammonia determinations. The saline group had no detectable ammonia in the urine. The reduction of arginine in the TPN solution from 0.65 to 0.1 g./100 ml. resulted in increasing ammonia levels in the urine. Plasma ammonia levels were the same for all groups (data not shown).

DETAILED DESCRIPTION OF THE PREFERRED EMBODIMENTS

The present invention, in its most general and overall scope, is directed to amino acid formulations, including amino acid formulations which contain the amino acid ornithine, methionine or arginine, useful in the stimulation of polyamine formation in the tumor-bearing individual. Methods are provided which utilize these amino acid formulations to improve the diagnostic reliability of polyamine level determination in cancer screening and cancer staging. Additionally, such formulations provide the capability of reducing toxicities associated with anti-tumor chemotherapy aimed at blocking polyamine production.

The present invention is also directed to an amino acid formulation for patients suffering from malignant disease. Additionally, methods are provided which utilize these amino acid formulations to reduce tumor growth rate. A process for preparing the subject amino acid formulations is also revealed.

a. Introduction

Polyamine production is associated with cell division. Increases in the intracellular levels of polyamines, particularly putrescine and spermidine, in the early phase of both normal and neoplastic cell proliferation are well documented. Conversely, a reduction in tumor burden is associated with a reduction of polyamine levels suggesting the potential use of polyamines as a biological marker of tumor growth. A substantial portion of circulating polyamines are carried in the RBC. Because the enzyme systems necessary to synthesize polyamines are not found in enucleated RBC, it is theorized that RBC are carriers of polyamines from sites of production to sites of conjugation and excretion.

The pathway for polyamine synthesis begins with L-ornithine. This natural amino acid, although not normally incorporated into proteins, is part of the urea cycle which metabolizes arginine to ornithine and ureas. Ornithine is converted by ornithine decarboxylase (ODC) to putrescine and $CO_2$, the rate-limiting step in the production of polyamines. Putrescine is converted to spermidine by spermidine synthetase in association with the decarboxylation of S-adenosylmethionine by S-adenosylmethionine decarboxylase. Spermidine is then converted to spermine by spermine synthetase, again in association with the decarboxylation of S-adenosylmethionine. Putrescine, spermidine and spermine represent the three primary polyamines.

It has been found that infusion of feeding solutions which contain precursors of polyamine metabolism, alter polyamine metabolism in the tumor-bearing host. One example is parenteral nutrition formulations which contain methionine, arginine and/or ornithine. Total parenteral nutrition formulations (TPN) are specific feeding solutions which generally contain higher amino acid concentrations than supplementary feeding solutions, for example. TPN is a technique used to intravenously feed malnourished cancer patients. These nutrient solutions generally contain concentrated glucose, crystalline amino acids, electrolytes and vitamins. The amino acid compositions of typical commercially available amino acid solutions are shown in Table 1. Each amino acid is purchased in crystalline form and compounded into amino acid solutions. Unique amino acid solutions are marketed for patients with kidney failure, liver failure and trauma patients. However, no special solutions yet exist for cancer patients.

Studies have shown that the polyamine biosynthetic pathways may be important in the development of amino acid solutions specific for cancer patients. An important consideration is the interaction between tumor polyamine production and a specific amino acid solution that may enhance RBC polyamines as tumor markers. It has been determined that administration of TPN solutions to patients with occult malignancies produce changes in polyamine levels compared with non-cancer patients while plasma CEA and creatine kinase-brain band levels did not change, indicating a specific increase in polyamine levels in tumor-bearing patients. Accordingly, the sensitivity and specificity of RBC polyamine measurements to detect occult disease may be enhanced with new amino acid solutions which include substrates for tumor polyamine production such as ornithine or arginine.

An additional important consideration in polyamine metabolism is the interaction between tumor polyamine utilization and specific amino acid solutions. It has been determined that administration of standard TPN solutions, which typically contain arginine, actually increase the rate of tumor growth while formulations with decreased standard arginine concentrations result in decreased tumor growth. It is hypothesized this data indicates arginine may act to promote tumor growth. Accordingly, the growth rate of tumors may be reduced with new amino acid solutions which decrease or eliminate this arginine substrate hypothesized to be utilized in tumor polyamine metabolism.

In recent years, chemotherapeutic agents that directly inhibit polyamine synthesis have been developed. Difluoromethylornithine (DFMO), one such drug, is an irreversible inhibitor of ODC and potentially can be given continuously with significant anti-tumor effects. This drug is relatively non-toxic to the host while producing inhibition of putrescine synthesis in tumors. Studies in a rat-tumor model demonstrate that DFMO infusion can produce a 90% decrease in tumor putrescine levels without suppressing peripheral platelet counts.

Although DFMO can effectively block tumor putrescine biosynthesis, the resultant anti-tumor effect is cytostasis and not cytotoxicity. For example, DFMO reduces the growth rate of an MCA sarcoma but does not produce tumor regression. This finding is consistent with reports of other investigators who showed that DFMO is a cytostatic agent. However, studies indicate that a significant role exists for DFMO agents, permitting the future development of combination chemotherapeutic regimens which incorporate DFMO.

Although the toxicity associated with DFMO therapy is not, in general, as severe as other types of chemotherapy, in limited clinical trials it has been found to promote a dose-related thrombocytopenia. Moreover, studies in rats have shown that continuous infusion of DFMO for 12 days significantly reduces platelet counts compared with controls. Other investigations have made similar observations in which thrombocytopenia is the major toxicity of continuous i.v. DFMO therapy. These findings suggest that DFMO may significantly inhibit ODC activity of the bone marrow precursors of megakaryocytes. It is contemplated by the present inventors that the formulations disclosed herein, in addition to promoting tumor polyamine production for diagnostic purposes, constitute specific antidotes to ODC-directed chemotherapy.

One means to reverse DFMO toxicity in the host is to infuse amino acid precursors of polyamine biosynthesis. Special amino acid solutions rich in ornithine or arginine made in accordance with the present invention can rescue the bone marrow from the toxic side effects of DFMO. For example, the addition of ornithine to feeder solutions in a rat-tumor model resulted in a significant reversal in the platelet suppression. Additionally, the constant infusion DFMO technology in a rat-tumor model permits the ability to test such new amino acid solutions in reducing DFMO induced thrombocytopenia. It is hypothesized that such solutions provide substrates which stimulate the production of polyamines in normal cells which are sensitive to ODC-directed chemotherapy, thus promoting recovery from toxic side effects of the drugs. Similarly, it is hypothesized that solutions containing polyamine precursors may serve to enhance ODC-directed chemotherapy against certain tumors, as adjuants to radiation therapy or may in themselves exhibit anti-tumor activity against some tumors.

Solutions prepared with essential amino acids+ornithine produce higher RBC putrescine levels compared with essential amino acids or essential amino acids+arginine. RBC and tumor spermidine and spermine levels are not affected to as great an extent by these solutions. The specific increases in putrescine levels may be explained by the proximity of certain amino acid components to the pathways of polyamine synthesis. Use of these new amino acid solutions could be important to detect occult malignancy following surgical resection. For example, colorectal carcinoma patients represent an ideal population to test the tumor-detecting capabilities of RBC polyamine levels enhanced by amino acid solutions. Such detection studies could be done, for example, two to three months postoperatively.

Use of a new amino acid solution to enhance the cancer detecting properties of blood polyamine measurements represents an improvement of currently available diagnostic methods. Breast and colorectal cancers represent possible malignancies where this may be applicable. Pathologic assessment of axillary lymph node involvement is the only means to predict risk of future metastatic disease in women with either clinical stage I or II disease. By increasing our ability to select patients with positive lymph node involvement, the benefits of adjuvant chemotherapy will be increased. Similar application can be made for patients with Dukes $B_2$ or $C_2$ rectal carcinomas. CEA measurements or diagnostic radiologic tests are not effective for selecting those patients with microscopic residual disease that can be treated by postoperative radiotherapy to the pelvis. Amino acid solutions with a novel amino acid such as ornithine could enhance polyamine detection of residual disease and, thereby, select patients who would benefit the most from postoperative adjuvant radiotherapy.

Enhanced cancer detection with polyamine measurements after TPN administration potentially represents considerable improvement over other tumor markers. Infusion of amino acid solutions rich in ornithine increase tumor polyamine production, thus elevating their levels in peripheral blood. Infusion of arginine or ornithine alone, that is, not in combination with one or all of the essential amino acids, has not produced elevated blood polyamine levels in the experimental tumor system.

b. Determination of polyamine Levels

Numerous techniques are known in the art for determining polyamine levels in aqueous biological samples such as urine and plasma. Generally, such techniques involve subjecting the aqueous sample to amino acid analysis by an automated amino acid analysis. In this manner, individual determinations of putrescine, spermidine and spermine may be made. More recently, enzymatic methods have been developed as disclosed in Japanese patents 8402700 and 8482099.

Although urine and plasma may be utilized for polyamine determinations in accordance with the present invention, it has been determined by the present inventors that red blood cell polyamine levels more accurately reflect tumor-related increases in polyamine production. Therefore, determination of RBC polyamines is a preferred method where accuracy is required, although this procedure is somewhat more involved. The following method is a representative RBC polyamine level determination.

After obtaining the blood sample by venipuncture, or some other suitable means, blood hematocrit is determined and the blood is centrifuged for 10 minutes at 500g. The plasma is removed for albumin determination and the remaining cells are washed with an equal volume of cold 0.9% NaCl and centrifuged at 200g for 15 minutes. The buffy coat is then carefully aspirated along with the supernatant and discarded. After thoroughly mixing the packed RBC, a 1.0 ml aliquot is extracted for polyamine analysis. While shaking continuously with a Vortex mixer, 2.5 ml of freshly prepared 6% trichloroacetic acid (TCA) is added followed by 60 ul of 100% TCA. This is done to avoid insufficient mixing if 100% TCA is added directly to RBC. The samples are mixed thoroughly for a minimum of 3 minutes and frozen at $-70°$ C. if further extraction steps are performed. The samples are thawed and centrifuged at $200 \times g$ for 15 minutes. The supernatant is then transferred to tubes containing 40 ul of concentrated HCl. The samples are washed twice with anhydrous ether and dried. The pellets are dissolved in 100 ul of 0.5 N HCl and centrifuged at 200g. The clear supernatant is then analyzed for polyamines using, for example, a Durrum D-500 amino acid analyzer.

In an additional embodiment, the patient's RBC polyamine level is determined both before and after administration of amino acid solutions. This allows the physician to both identify the "reactivity" of the patient's polyamine level and to further compare with normal profiles. The following example demonstrates the use of total parenteral nutrition solutions to detect recurrent malignant disease.

Example I: Detection of Recurrent Malignant Disease By Polyamine Analysis in Patients Receiving Total Parenteral Nutrition This study was performed to demonstrate that total parenteral nutrition (TPN) results in significant increases in erythrocyte (RBC) polyamine levels in patients with clinically occult recurrent malignant disease. TPN was administered preoperatively to six noncancer patients and seven patients who had a history of curative operation for malignant disease and, after receiving TPN, were found to have recurrent disease. RBC putrescine (PUT), spermidine (SPD), and spermine (SPM) were determined before and after preoperative TPN in each patient. Plasma carcinoembryonic antigen (CEA) and creatine kinase brain band (CK-BB) were also measured during the study as controls. Mean length ($\pm$S.E.) of preoperative TPN for the noncancer group and the group harboring occult recurrent disease was $8.4\pm2.9$ days and $9.6\pm3.6$ days, respectively, There were no significant changes in RBC polyamine and plasma CEA and CK-BB levels in the noncancer group after TPN. Those patients with occult malignant disease had significant increases in RBC PUT and PUT/SPD ratio (p 0.05) during TPN, while RBC SPD and SPM and plasma CEA and CK-BB did not change. The data indicates that short-term TPN can enhance the use of polyamine measurements as markers of recurrent malignant disease.

PATIENT POPULATION

Patients who required preoperative TPN in order to restore or prevent nutritional deficits before an operative procedure were entered into this study. Patients who received chemotherapy or radiation therapy or underwent an operative procedure within three months of this study were excluded. Women with active ovulatory cycles were also excluded. The only treatment given during preoperative TPN was nutritional therapy. All patients had normal renal function (plasma creatinine less than 1.4 mg/dL and BUN values less than 25 mg/dL) and normal liver function (serum bilirubin less than 1.4 mg/dL) as prerequisites for entry into the study. This study was conducted with the approval of the Human Surveillance Committee of M.D. Anderson Hospital and the informed consent of the patient.

There were six patients who required preoperative TPN and who were free of malignant disease, as documented by exploratory laparotomy, histologic evaluation of the respected specimens, and length of disease-free status (greater than five years). There were seven patients with clinically occult recurrent malignant disease during their course of preoperative TPN. These patients had had either a "curative" operative procedure or had a suspicious lesion that could not be proven as recurrent malignant disease by diagnostic evaluation, which included roentgenographic and endoscopic studies. Disease status was determined by exploratory laparotomy following preoperative TPN or by follow-up clinic visits.

NUTRITIONAL REGIMEN

TPN solutions consisted of 50% glucose (500 ml), 10% crystalline amino acids (500 ml), NaCl (40–60 mEq/L), KCl (20–40 mEq/L), $KH_2PO_4$ (10–15 mEq/L), Ca gluconate (4.5 mEq/L), $MgSO_4$ (10–15 mEq/L), MVI-12 (10 ml), and trace elements (2 ml). A 10% soybean oil emulsion (500 ml) was administered biweekly. TPN solutions were administered continuously through a central venous catheter at a rate of 30–50 calories/kg body weight/day and 2.0–3.0 g amino acid/kg body weight/day. Fluid and electrolyte balance was monitored every Monday, Wednesday, and Friday.

STUDY DESIGN

Each patient was hospitalized for 7 to 10 days of preoperative TPN. Before TPN was started, venous blood (7 ml in a heparin-coated tube) was obtained. After completion of preoperative TPN and on the day before the operative procedure, a second venous blood sample was obtained. RBC polyamine determinations and plasma CEA and CKBB measurements were done before and after preoperative TPN for each patient. In this manner, each patient served as his or her own control in determining the effect of TPN on RBC polyamines and plasma CEA and CK-BB levels. Analysis of data was done by a paired Student's t-test, comparing levels before and after TPN within the noncancer and cancer groups.

POLYAMINE, CEA AND CK-BB DETERMINATIONS

RBC putrescine, spermidine, and spermine levels were measured by high performance liquid chromatography using a Durrum D-500 amino acid analyzer, (Dionex Corp., Palo Alto, CA.) as described above. Plasma CEA was determined by an enzyme immunoassay procedure kit (Abbott Laboratories, North Chicago, ILL) and plasma CK-BB was measured with a radioimmunoassay method (Mallinkrodt, Inc., St. Louis, MO.).

The clinical history of each patient is shown in Table II. The six noncancer patients received preoperative TPN for 8.4±2.9 days (mean±S.E.). Patients #4 and #5 were both studied twice, six and twelve months apart, because of two separate episodes of weight loss induced by short gut syndrome. This accounts for the eight determinations of sequential polyamine measurements for this group. There were seven patients with clinically occult malignant disease. Three patients had recurrent disease at laparotomy immediately following preoperative TPN. The other four patients developed recurrent disease at three months to two years after the study. The mean length of TPN for this group was 9.6±3.6 days. Mean weight loss, based on usual body weight, was 7.1±1.1% TPN was started. Preoperative TPN was given without infectious or metabolic complications.

TABLE II

| Age | Sex | Diagnosis |
|---|---|---|
| *Patients with Occult Malignant Disease* | | |
| 59 | F | Recurrent bladder carcinoma 9 mos. after TPN |
| 58 | F | Recurrent esophageal carcinoma 3 mos. after TPN |
| 49 | M | Recurrent pancreatic carcinoma 7 mos. after TP |
| 60 | M | Recurrent esophageal carcinoma discovered at laparotomy |
| 40 | M | Recurrent esophageal carcinoma discovered at laparotomy |
| 48 | F | Gastric carcinoma discovered at laparotomy |
| 78 | F | Recurrent colon carcinoma 24 mos. after TPN |
| *Patients with Benign Disorders* | | |
| 50 | F | Benign esophageal stricture |
| 55 | F | Benign gastric ulcer |
| 30 | F | Pseudointestinal obstruction |
| 20 | F | Chronic radiation enteritis and short gut syndrome |
| 51 | M | Chronic radiation enteritis and short gut syndrome |

TABLE II-continued

| Age | Sex | Diagnosis |
|---|---|---|
| 71 | F | Benign gastric ulcer |

*patients were studied twice for a total of eight sequential polyamine studies for the noncancer group.

Figure 1:
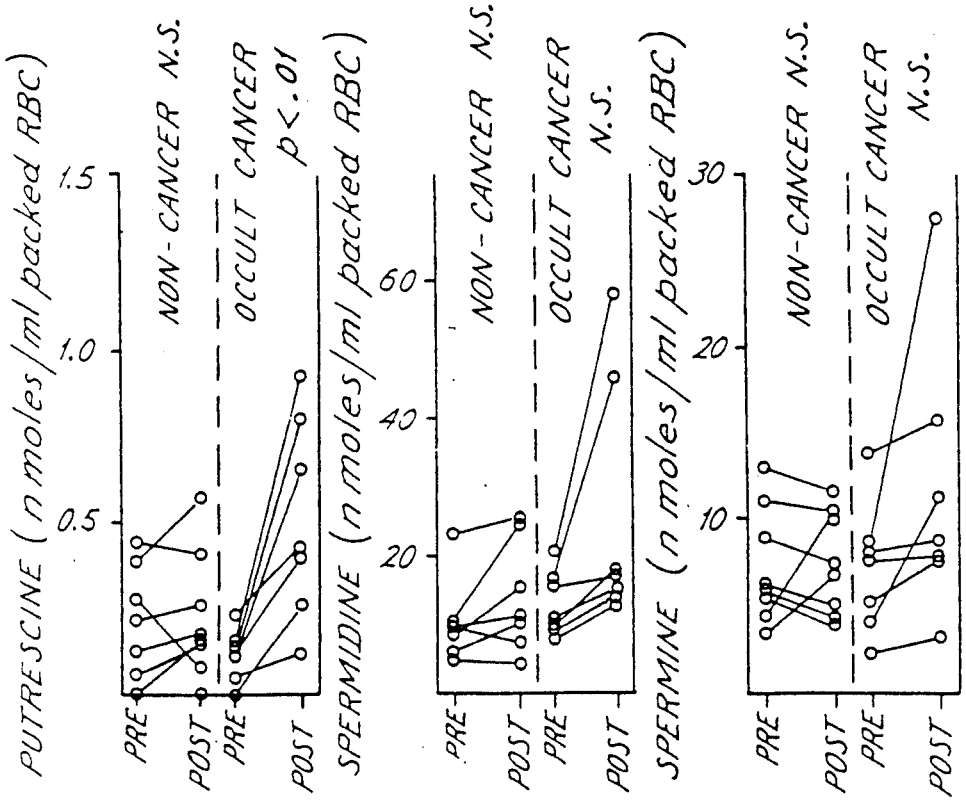
FIG. 1. Graphs demonstrate changes in RBC putrescine, spermidine, and spermine levels in non-cancer patients and patients with clinically occult malignant disease during TPN (total parenteral nutrition) therapy. PRE indicates RBC polyamine levels before preoperative TPN was started, and POST indicates levels after 7-10 days of preoperative TPN but before surgery. N.S. indicates not significant.
Figure 2:
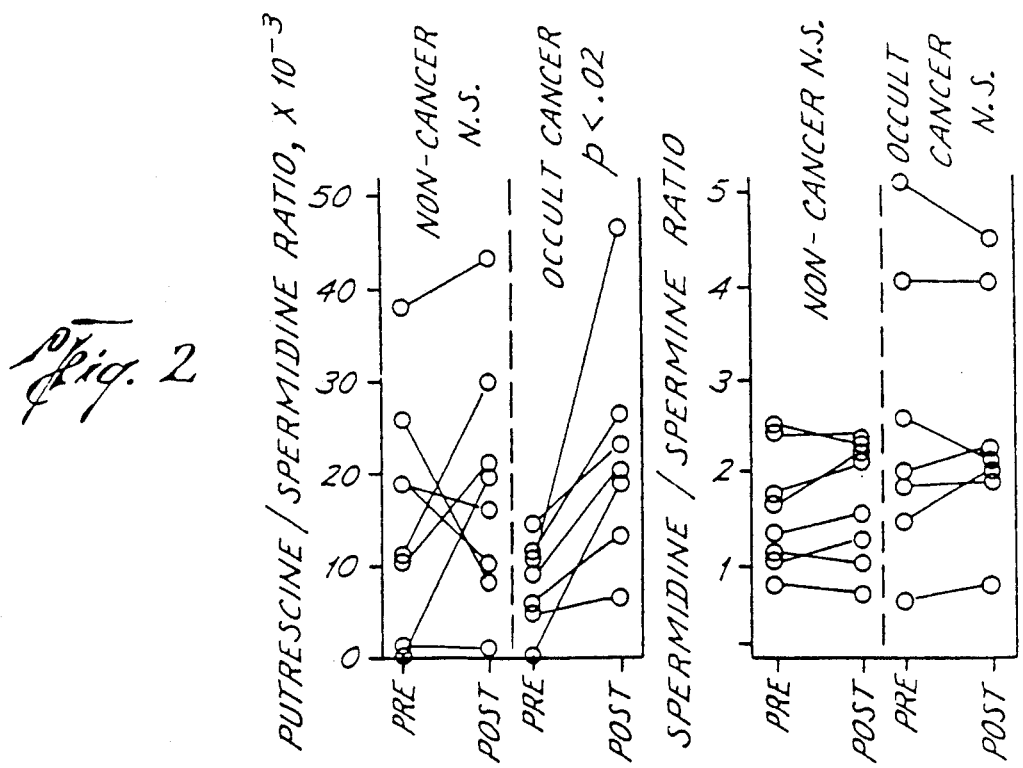
FIG. 2. Graphs demonstrate changes in RBC putrescine: spermidine and spermine: spermine ratios in non-cancer patients and patients with clinically occult malignant disease during TPN. PRE indicates RBC polyamine ratios before preoperative TPN was started and POST indicates ratios after 7-10 days of preoperative TPN but before surgery. N.S. indicates not significant.

Polyamines could not be detected in TPN solutions. Changes in RBC count ($\times 10^6$/mm$^3$) were similar for both groups with a mean decrease of 4.3% during TPN. FIG. 1 shows the changes in RBC putrescine, spermidine, and spermine for both groups. Eight determinations in six noncancer patients showed no significant increases in RBC polyamine levels during TPN. The patients with clinically occult malignant disease had a significant increase in RBC putrescine levels ($p<0.01$), while RBC spermine levels increased but not significantly. There was a trend toward higher, but not significant, spermidine levels in this group ($p<0.7$).

Changes in RBC putrescine: spermidine and spermidine: spermine ratios during TPN for both groups are shown in FIG. 1. The spermidine: spermine ratio did not change for either group. The patients with clinically occult malignant disease had a significant increase in the putrescine: spermidine ratio, while the noncancer group did not. Plasma CEA and CK-BB levels did not increase significantly during TPN in either group of patients as shown in Table III.

TABLE III

Plasma CEA and CKBB Data During TPN[a]

| | | Plasma CEA (ng/ml)[b] | | Plasma CKBB (ng/ml)[b] | |
|---|---|---|---|---|---|
| | n | Pre | Post | Pre | Post |
| Noncancer | 6 | 2.9 ± 1.6 | 2.8 ± 1.4 | 3.6 ± 2.1 | 3.5 ± 2.4 |
| Occult Cancer | 4 | 2.4 ± 2.0 | 5.0 ± 4.9 | 1.9 ± 0.5 | 1.6 ± 0.3 |

[a]Plasma carcinoembryonic antigen (CEA) and creatine kinase brain band (CKBB) were determined before (Pre) and after (Post) preoperative TPN in noncancer patients and patients with clinically occult malignant disease. Normal values for CEA are 0-3 ng/ml (non-smokers) and 0-6 ng/ml (Smokers).
[b]Values represent ± SD The previous example demonstrates that two procedures may enhance the value of polyamines as markers of recurrent malignant disease. First, using each patient as his or her own control, polyamine measurements were determined at two different time points. Second, in between the two measurements, a hypertonic glucose-amino acid solution was infused. The combination of these two procedures seemed to enhance the detection of malignant disease with polyamine measurements.

Increases in RBC putrescine during TPN are thus related to either increased substrate levels with constant tumor ODC activity or increased tumor ODC activity and subsequent proliferation. In addition it appears that increases in RBC polyamines during TPN in cancer patients are related to tumor proliferation.

An important concept of polyamine metabolism is that tumors may have a greater requirement for polyamine synthesis, whereas normal tissues may have a lesser requirement for polyamines because of their controlled growth behavior. By providing nutrient substrates, TPN may be increasing polyamine production in tumor cells that then excrete these products into the extracellular space and are absorbed by RBC.

In particular, the TPN solution utilized in the previous example was Travasol 10%, whose amino acid composition is displayed in Table 1. Travasol 10% is used in compounding a feeding solution for general administration in patients with benign or malignant diseases. However, the present inventors contemplate that any of the commercially available parenteral amino acid formulations will function in the practice of the present invention. In fact, amino acid formulations may be designed which include a wide range of amino acid concentrations and combinations. For example, parenteral solutions with up to three times the amino acid concentration of commercial TPN solutions would not be considered toxic and would therefore be functional in the present invention. It appears that the only requirement for practicing the present invention is that such solutions contain one or more of the essential amino acids and either ornithine or arginine, or both, with ornithine being preferred.

Example II: Feeding Solutions Containing Ornithine

Ornithine has been combined with essential amino acids and utilized in a rat tumor model to demonstrate its potential utility in man. Rats having been implanted with a methylcholanthrene (MCA)—induced tumors received continuous infusion of one-fold diluted Nephramine 5.4% in combination with either arginine or ornithine. Polyamine levels were determined both before and after feeder solutions infusion in control no arginine or ornithine experimental (tumor-bearing rats given solutions with ornithine or arginine) and sham or chow-fed rats.

Male Fisher 344 rats were purchased from Timco Harlan-Sprague-Dawley (Houston, Texas). All rats were allowed a 7-day acclimation period with chow (Purina 5001) and water ad libitum. A methylcholanthrene-induced fibrosarcoma (0.17 g) was implanted as a brei into the right flank under anesthesia and the animals were fed a chow diet for 21 days. When the tumors were at least 1.0 cm in width, two-dimensional measurements with calipers were instituted and the equation, length (cm)×(width [cm])$^2$×$\frac{1}{2}$ = grams of tumor tissue, was used to estimate tumor weight. When tumor weight reached 14±3 g (21 days of chow diet), the animals were randomized into three groups by tumor weight and under anesthesia a Silastic central venous catheter was placed in the superior vena cava through an internal jugular vein cutdown. The animals were then allowed to recover overnight and continuous infusions were started the next morning. Essential amino acids-+arginine rats (E+A rats) received a continuous infusion of 500 ml 60% glucose+500 ml 5.4% Nephramine with 0.58 g/100 ml or arginine added for 6 days. Essential amino acids+ornithine rats (E+O rats) received 500 ml 60% glucose+500 ml 5.4% Nephramine with 0.44 g/100 ml of ornithine added. The ornithine and arginine were added at equimolar concentrations. Nephramine is a parenteral amino acid solution consisting of eight essential amino acids and histidine. After 6 days of continuous infusion, the animals were sacrificed by aortic bleeding. Liver and tumor were excised and weighed and kept frozen at −70° C. until assays were done. Only viable, nonnecrotic tumor tissue was saved and assayed.

Preparation of tumor tissue for polyamine assay was done in the following manner. Tumor tissue weighing 0.5 to 1.5 g was cut into small pieces and put into a disposable tube (16×100 mm). Ice-cold 4% sulfosalicylic acid was then added at 2 ml/g wet tissue. This mixture was homogenized in an ice bath for 40 seconds using the Brinkman Polytron homogenizer (P10ST generator set at 8.5). The suspension was centrifuged at 100,000g for 30 minutes and the resulting clear supernatant was analyzed for polyamines on a Durrum D-500 amino acid analyzer.

Statistical analyses were done with Student's t test (one tail). RBC determinations were performed as described above; blood was obtained by aortic puncture.

The results are demonstrated in Table IV. As Table IV indicates, levels of putrescine within the tumors were increased approximately three fold whereas levels of all three polyamines were significantly increased in the rat's RBC's. In both cases, ornithine functioned better than arginine, but both appeared to promote an increase in tumor-related levels. Comparison of these valves from tumor-bearing rats to non-tumor bearing would demonstrate an even more substantial difference in relative polyamine levels.

TABLE IV

| Nutritional Regimen[1] | n | Tumor Weight[1] | | |
|---|---|---|---|---|
| | | Initial | Final | % Change[2] |
| Chow | 5 | 13.3 ± 2.6 | 32.9 ± 5.3 | 134 ± 32 |
| E | 4 | 14.0 ± 2.8 | 35.7 ± 6.9 | 135 ± 42 |
| E + A | 6 | 10.5 ± 2.2 | 25.7 ± 3.4 | 153 ± 68 |
| E + O | 7 | 11.1 ± 2.2 | 24.4 ± 4.9 | 123 ± 34 |

| Tissue | Nutritional Regimen | n | Polyamine Levels | | |
|---|---|---|---|---|---|
| | | | Putrescine | Spermidine | Sperm |
| Erythrocyte | Chow | 5 | 0.91 ± 0.21 | 71 ± 57 | 6.1 ± 4.1 |
| | E | 4 | 1.42 ± 0.32 | NA | NA |
| | E + A | 6 | 1.60 ± 0.52 | 69 ± 45 | 6.5 ± 2.6 |
| | E + O | 7 | 1.85 ± 0.36 | 125 ± 9 | 10.9 ± 3.3 |
| Tumor | Chow | 5 | 46.9 ± 12.2 | 797 ± 80 | 392 ± 21 |
| | E | 4 | 22.9 ± 4.4 | 901 ± 39 | 480 ± 35 |
| | E + A | 6 | 50.5 ± 13.3 | 871 ± 69 | 409 ± 36 |
| | E + O | 7 | 73.6 ± 17.1 | 919 ± 90 | 415 ± 30 |

[1]Fibrosarcoma, growing s.c.
[2]% increase in tumor weight.

Additionally, the previous example demonstrates that 450 mg of ornithine for every 100 ml of the amino acid formulation functions satisfactorily and continuous infusion of such solutions which posed no toxicity problems. It is contemplated that amino acid solutions ranging from 50 mg up to 2 g per 100 ml of solutions (with between 50 and 750 mg/100 ml being a preferred range for arginine and ornithine) should function satisfactorily without loss of appreciable activity or increased toxicity. However, for the detection of microscopic tumors and as an antidote to ODC-directed antitumor therapy, higher concentrations of ornithine are suggested.

Another experiment which utilized formulations containing amino acid precursors of RBC polyamines, compared the response of tumor-bearing rats (TB) to non tumor-bearing rats (NTB). The study was performed basically in the manner described above with the following indicated differences. Fibrosarcoma-bearing (TB) and non-tumor being F344 rats (NTB) were infused with either a typical feeding solution (30% glucose+5% essential amino acids), with essential amino acids (19 g/L, 30% glucose) plus arginine at 19.5% g/1 (E+A). Chow rats (C) were fed chow with no i.v. infusion.

TABLE V

| Treatment | N | NTB PUT | N | WT. | PUT | N | TB WT | PUT |
|---|---|---|---|---|---|---|---|---|
| C | 13 | .39 ± .10 | 5 | 13 ± 3 | .7 ± 10 | 6 | 37 ± 10 | 1.2 ± 0.2 |
| E | 9 | .41 ± .07 | 6 | 15 ± 2 | .9 ± .3 | 4 | 36 ± 7 | 1.4 ± 0.3 |
| E + A | 5 | .62 ± .22 | 8 | 11 ± 3 | 1.9 ± .3 | 2 | 51 ± 22 | 5.0 ± 2.7 |

Where N is the number of rats included in the study, PUT is RBC levels (nm/g/ml, means±SD) of putrescine determined by HPLC.

As demonstrated in Table IV, the increase in RBC putrescine levels in NTB rats following administration of feeding solutions which included a specific putrescine precursor (arginine) was significantly greater ($p<0.05$) than those receiving chow or essential amino acids only. However, the RBC putrescine level of TB rats receiving E+A was significantly greater than any other group in the study. It should also be noted that increased putrescine levels were found to be proportional to tumor weight.

c. Reduction of DFMO Induced Thrombocytopenia

Figure 3:
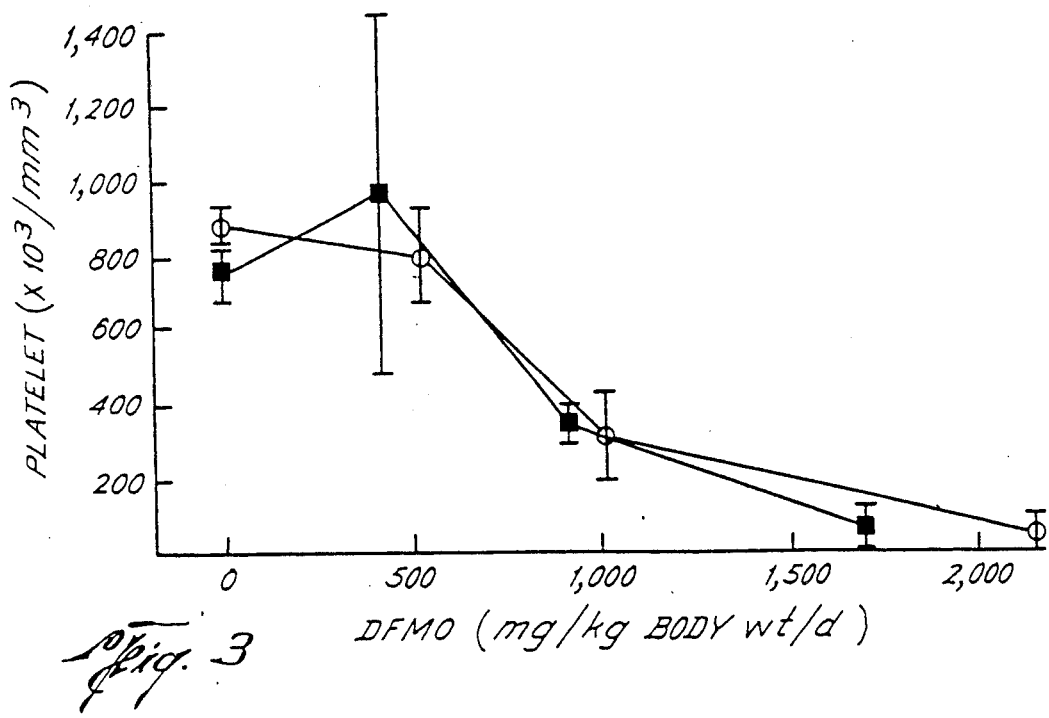
FIG. 3. Platelet counts plotted against dose of DFMO given as a continuous i.v. infusion for 12 days in tumor-bearing (O) and non-tumor-bearing rats (o). Bars indicate standard deviation. As the dose of DFMO increases, there is significant platelet suppression. This experiment was done to determine if simultaneous ornithine infusion could block platelet suppression.

Animal and clinical studies have shown that the major host toxicity associated with the continuous infusion of DFMO is thrombocytopenia (Ota et al. (1986), Int. J. Cancer, 38:245; see also FIG. 3 herein). In the above described rat model, a continuous infusion of DFMO was given through a central venous catheter. Non-tumor-bearing and tumor-bearing rats received continuous i.v. DFMO for 12 days. The DFMO doses typically employed were 500 mg, 1000 mg, and 2000 mg per kg body wt per day. Although there was histological evidence of small intestinal mucosal atrophy at these doses, no significant clinical toxicity was seen during the 12 day study. However, dose related thyrombocytopenia was observed, as shown in FIG. 3. White cell count and hematocrit changes were not significantly altered by DFMO administration.

Figure 4:
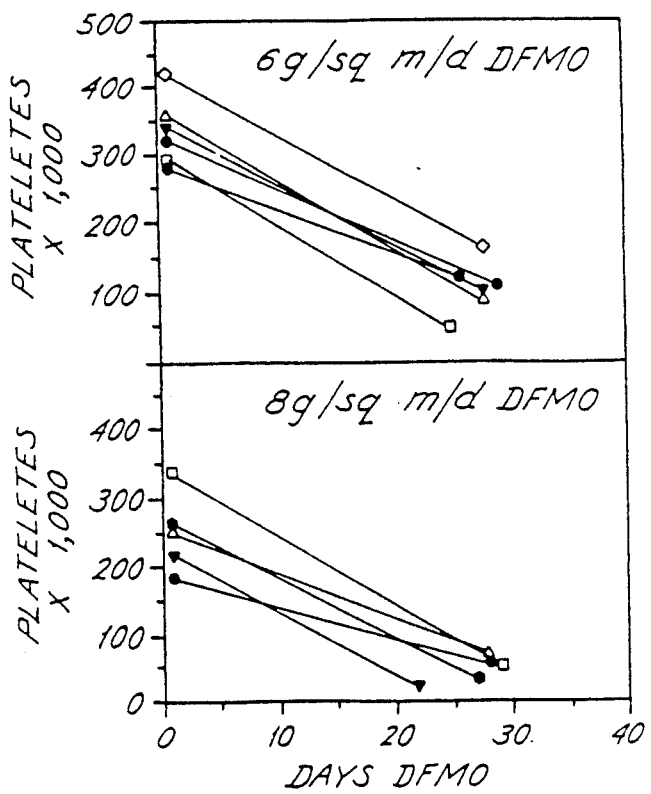
FIG. 4. Platelet counts plotted against days of continuous i.v. DFMO infusion in patients with advanced colorectal carcinoma. The upper graph shows the platelet suppression at 6 g DFMO/sq m/d. The lower graph depicts the platelet suppression at 8 g DFMO/sq m/d. Each course of infusion is shown by two points representing day 1 of infusion and day 22 to 28 when DFMO was discontinued. The paired points are connected by a straight line. The data show that platelet suppression is the major limiting host toxicity of DFMO given as a continuous infusion. The simultaneous infusion of ornithine with DMFO may inhibit platelet toxicity.

Clinical studies with patients undergoing DFMO therapy have shown that the continuous infusion of DFMO for 28 days also produced significant clinical thrombocytopenia. Eleven cycles of 28 day DFMO infusion have been administered to 7 patients at doses of either 6 or 8 g DFMO/m²/day. As shown in FIG. 4, the platelet suppression was significant at both doses. There was significantly greater platelet suppression at the 8 g dose as compared with the 6 g dose. Significant suppression of the hematocrit was also noted with a trend toward dose related suppression. White cell count was not affected by either dose. There was no incidence of nausea, vomiting or diarrhea. There were two patients who experienced decreased hearing acuity at 8 h DFMO/m²/day. All toxicities resolved spontaneously within two weeks of discontinuing the DFMO infusion.

The following study was designed to determine if the simultaneous administration of ornithine with DFMO would reduce thrombocytopenia. Central venous catheters were inserted into Fisher 344 male rats. The animals received approximately 1500 mg DFMO per kg body wt per day as a continuous i.v. infusion. Ornithine HCl (Ajinomoto, Ltd., New York, NY) was added to the saline solutions at a final concentration of 3.3 mmol/100 ml. This concentration is equimolar to the arginine concentration in 10% Travasol. After 12 days of infusion the rats were sacrificed and platelet counts were determined in peripheral blood.

Table IV shows the results of this experiment. There were 3 treatment groups consisting of saline, DFMO and DFMO with ornithine. As shown in Table VI, the simultaneous administration of ornithine with DFMO blocked platelet suppression. DFMO alone resulted in a significant decrease in platelet count as compared with the saline treatment.

TABLE VI

Influence of Ornithine Co-administration On DFMO-Induced Thrombocytopenia in the Rat

| Treatment | n | Platelets ($\times 10^3$/cu. mm) |
|---|---|---|
| Saline | 3 | 780 ± 253 |
| DFMO[b] | 5 | 409 ± 127 |
| DFMO + Orn[c] | 6 | 958 ± 195[d] |

[a]Fischer 344 male rats received a continuous infusion of saline, DFMO or DFMO + ornithine for 12 days. All rats received chow and water ad libitum.
[b]DFMO dose = 1444 ± 73 mg/kg/d.
[c]DFMO dose = 1429 ± 85 mg/kg/d; Ornithine dose = 436 mg/100 ml or 3.3 mmoles/100 ml infusion.
[d]Mean differs significantly compared with DFMO treated rats.

These results demonstrated that parenteral administration of polyamine precursors can significantly reduce DFMO induced platelet toxicity. The results further indicate that, at least in the animal system studied, a concentration of approximately 33 mM is adequate to prevent or reduce the occurrence of thrombocytopenia. However, it is contemplated that virtually any non-toxic amount of polyamine precursor can be employed. Moreover, the results indicate that polyamine precursors may be administered alone and do not require the presence of additional amino acids.

d. Inhibition of tumor growth

An important consideration in developing a tumor-inhibiting formulation is the interaction between tumor versus host polyamine utilization and specific amino acid solutions. It has been determined that administration of standard TPN solutions to patients with occult malignancies produce an elevation in polyamine levels compared with non-cancer patients. Consequentially, this phenomenon has been used in the formulation of specific amino acid solutions for detecting the presence of tumors in patients.

Generally, reduced levels of tumor polyamines have been correlated to a decrease in tumor growth rate. However, infusion of amino acid solutions rich in ornithine will increase polyamine levels despite the decrease in tumor growth rate elicited. It is hypothesized that this anomoly may be explained by ornithine's status as a non-essential amino acid. Ornithine is not incorporated into the synthesis of proteins, thus possibly explaining the lack of any increase in tumor growth exhibited in animals receiving formulations rich in ornithine. Additionally, ornithine is only passively taken up by the cells, compared to the active uptake of essential amino acids such as arginine. Also, the high polyamine levels might be explained by ornithine's status as a polyamine precursor. The reasons for the relatively large standard errors in the ornithine group tumor studies are currently being investigated to determine the actual role of ornithine in tumor growth.

In recent years, several studies in animal-tumor models have shown that nutritional therapy can result in tumor growth and, in some cases, accelerate growth. For some tumors, tumor growth can also occur during host starvation, emphasizing that tumors will obtain either exogenous or endogenous nutrients for their energy needs and biosynthetic pathways. (Sauer, L.A., Nagel, W.D., Dauchy R.T., et al. (1986), *Cancer Res.*, 46:3469.

One strategy in approaching the problem of host-tumor competition for nutrients is to formulate an amino acid regimen that does not include substrates that enhance tumor growth. The present invention addresses this strategy by defining specific combinations and concentrations of amino acids that decrease the presence of amino acids that are polyamine biosynthetic precursors hypothesized as being responsible for stimulating tumor growth. A formula which includes a non-toxic, pharmacologically acceptable amount of the amino acids together with ornithine and citrulline and less than 0.45% by weight final concentration of arginine is one formula which has been found to inhibit tumor growth.

It is hypothesized that arginine is the specific amino acid responsible for stimulating tumor growth. Arginine is commonly found in general parenteral amino acid formulas and by weight (mg/100 ml) makes up 10% of the amino acid composition before formulation. After formulation of such a general parenteral amino acid formula, arginine comprises about 1% by weight final concentration (1.0 g./100 ml). Applicants' solutions decrease or eliminate this standard arginine content. Also, ornithine and citrulline are not present in any commercially available parenteral amino acid formula. These amino acids are necessary to Applicant's formulas. Thus, standard solutions could not conveniently be used in their commercially available concentrations to practice the Applicants methods or formulations.

The subject invention includes several formulations comprised of various mixtures of essential and non-essential amino acids obtained in crystalline form. Arginine may or may not be included in the particular formula. A sufficient quantity of citrulline or ornithine is then added so as to constitute greater than about 0.5% by weight concentration of the solution upon the addition of a suitable liquid medium. One preferred liquid medium is a glucose solution. This glucose solution may range from 5% to 70% glucose in the present formulations. Patient nutritional support formulations are commonly constituted in such glucose solutions. Desirable relative internal proportions of the included amino acids are defined by the following Table VII for every 100 milliliters of the formulation.

TABLE VII

| Amino Acids | Mg./100 ml. formulation |
| --- | --- |
| Essential Amino Acids | |
| leucine | 250 to 1400 mg |
| isoleucine | 200 to 1400 mg |
| valine | 200 to 1250 mg. |
| phenylalanine | 100 to 900 mg |
| methionine | 50 to 850 mg |
| lysine | 150 to 750 mg |
| histidine | 85 to 500 mg |
| threonine | 100 to 550 mg |
| tryptophan | 50 to 200 mg |
| Non-essential Amino Acids | |
| alanine | 200 to 3500 mg |
| glycine | 250 to 2000 mg |
| proline | 100 to 1500 mg |

TABLE VII-continued

| Amino Acids | Mg./100 ml. formulation |
| --- | --- |
| serine | 5 to 650 mg |
| tyrosine | 30 to 60 mg |

It will be understood that in addition to the amino acids, the formulation may include preservative agents.

The preparations may be advantageously prepared in the form of sterile aqueous solutions adapted for intravenous administration. In accordance with known practice for such solutions, the malignant disease amino acid solutions will be sterile, pyrogen free, and at a suitable pH for parenteral administration.

Specific formulations for practicing the present invention are set out in the following examples.

EXAMPLE III

A sterile, non-pyrogenic, stable solution suitable for parenteral administration to patients with malignant disease is prepared from pure crystalline amino acids, which are dissolved in a glucose solution (5% to 70%) in the following concentrations:

| Amino Acids | Mg./100 ml. formulation |
| --- | --- |
| leucine | 250 to 1400 mg |
| isoleucine | 200 to 1400 mg |
| valine | 200 to 1250 mg. |
| phenylalanine | 100 to 900 mg |
| methionine | 50 to 850 mg |
| lysine | 150 to 750 mg |
| histidine | 85 to 500 mg |
| threonine | 100 to 550 mg |
| tryptophan | 50 to 200 mg |
| tyrosine | 30 to 60 mg |

This formulation is arginine-free.

To the foregoing formulation is added a sufficient quantity of citrulline or ornithine so as to constitute about 1% by weight of the formulation. At least one of the following non-essential amino acids is then added in the following concentration:

| Amino Acids | Mg./100 ml. formulation |
| --- | --- |
| alanine | 200 to 3500 mg |
| glycine | 250 to 2000 mg |
| proline | 100 to 1500 mg |
| serine | 5 to 650 mg |

The solution is then filtered into appropriate containers for intravenous fluids and steam sterilized at 250° F. for 10 minutes. To prepare for administration, the volume is then brought to the desired feeding solution volume with an additional volume of glucose solution and kept cool. The solution is then administered to the patient intravenously (i.v.).

EXAMPLE IV

If a formulation of amino acids for patients with malignant disease is desired which contains ornithine, but is citrulline free, the formula as outlined in Example III can be utilized. Ornithine will be added to constitute greater than about a 0.5% by weight concentration of the formulation, and no citrulline will be added. The same proportions of the essential and non-essential amino acids (leucine, isoleucine, valine, phenylalanine, lysine, valine, isoleucine, threonine, tryptophan, histidine, tyrosine, alanine, glycine, proline and serine) will be present; and the solution prepared in the same manner. This formulation is arginine-free.

EXAMPLE V

Following the procedure of Example IV, an alternate amino acid formulation with arginine for patients with malignant disease is prepared from the following pure crystalline amino acids and in the following concentrations:

| Amino Acids | Mg./100 ml. formulation |
|---|---|
| Essential Amino Acids | |
| leucine | 250 to 1400 mg |
| isoleucine | 200 to 1400 mg |
| valine | 200 to 1250 mg. |
| phenylalanine | 100 to 900 mg |
| methionine | 50 to 850 mg |
| lysine | 150 to 750 mg |
| histidine | 85 to 500 mg |
| threonine | 100 to 550 mg |
| tryptophan | 50 to 200 mg |
| Non-essential Amino Acids | |
| alanine | 200 to 3500 mg |
| glycine | 250 to 2000 mg |
| proline | 100 to 1500 mg |
| serine | 5 to 650 mg |
| tyrosine | 30 to 60 mg |

This mixture of essential and non-essential amino acids is then dissolved in distilled water. To the foregoing formulation is added a sufficient quantity of arginine so as to constitute less than about 0.10% by weight of the final formulation. Ornithine or citrulline is then added so as to constitute at least about 0.50% by weight of the final formulation. The volume is then brought to the desired volume with a glucose solution (5% to 70%). The solution is then filtered into appropriate containers for intravenous fluids and steam sterilized at 250° F. for 10 minutes.

To prepare the feeding solution, the stock formula above is then added to an appropriate volume of glucose solution (5% to 70%) so as to constitute a final arginine concentration of less than about 0.10% by weight.

EXAMPLE VI

If a formulation of amino acids for patients with malignant disease is desired which contains alanine as the 15 non-essential amino acid of choice, the formula as outlined in Example III can be utilized. The same proportions of the essential amino acids (leucine, isoleucine, valine, phenylalanine, methionine, lysine, histidine, threonine, tryptophan and tyrosine) will be present; and the solution prepared in the same manner. Alanine will then be included at about a 1% by weight final concentration of the formula upon the addition of a glucose solution to the prepared stock.

EXAMPLE VII

A sterile, non-pyrogenic, stable solution suitable for parenteral administration to patients with malignant disease is prepared from pure crystalline amino acids, which are dissolved in distilled water in the following concentrations:

| Amino Acids | Mg./100 ml. formulation |
|---|---|
| Essential Amino Acids | |
| leucine | 250 to 1400 mg |

-continued

| Amino Acids | Mg./100 ml. formulation |
|---|---|
| isoleucine | 200 to 1400 mg |
| valine | 200 to 1250 mg. |
| phenylalanine | 100 to 900 mg |
| methionine | 50 to 850 mg |
| lysine | 150 to 750 mg |
| histidine | 85 to 500 mg |
| threonine | 100 to 550 mg |
| tryptophan | 50 to 200 mg |
| Non-essential Amino Acids | |
| alanine | 200 to 3500 mg |
| glycine | 250 to 2000 mg |
| proline | 100 to 1500 mg |
| serine | 5 to 650 mg |
| tyrosine | 30 to 60 mg |

To the foregoing formulation is added a sufficient quantity of ornithine so as to constitute about greater than 0.5% by weight of the final formulation. Also, citrulline is to be added so as to constitute about 0.01 to 2% by weight of the final formulation. Arginine is to be included so as to constitute a less than about 0.10% by weight concentration of the final formulation. The solution is then filtered and filled into appropriate containers for intravenous fluids and steam sterilized at 250° F. for 10 minutes. To prepare the actual feeding solution from the above stock, the volume is then brought to the desired volume with a glucose solution so as to constitute at least a 0.50% by weight ornithine and less than about 0.10% arginine.

Figure 5:
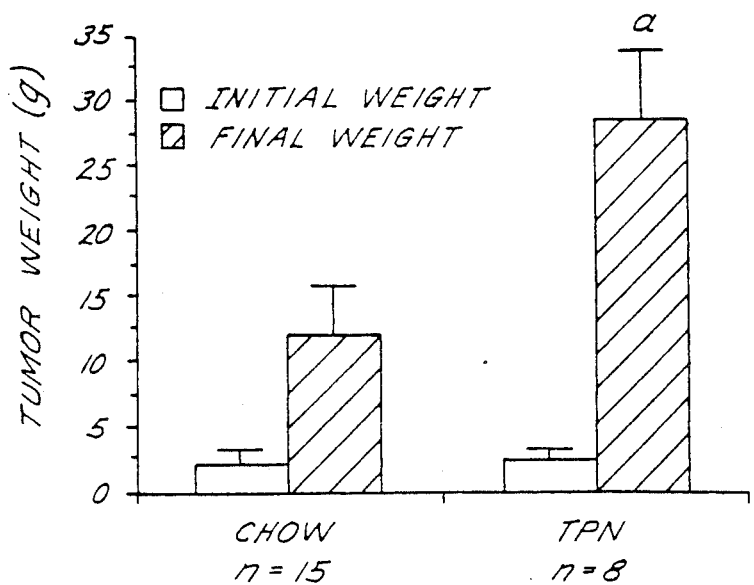
FIG. 5. TPN-induced tumor growth during the plateau phase of colon carcinoma. Fisher 344 rats with 3 g transplantable colon tumors growing s.c. in the R flank were randomized to 2 groups and a central venous catheter was inserted. CHOW received i.v. saline and oral chow ad libitum for 12 days. TPN consisted of 500 ml D50W +500 ml 10% Travasol (general amino acid solution) and was administered for 12 days to the other group. Note that TPN was administered during the period of time when the tumor was entering the plateau phase of growth. The final tumor weight (after 12 days TPN) for the TPN group was significantly greater than the CHOW final tumor weight ($P<0.05$). a=$P<0.05$ compared with CHOW final tumor weight.
Figure 6A:
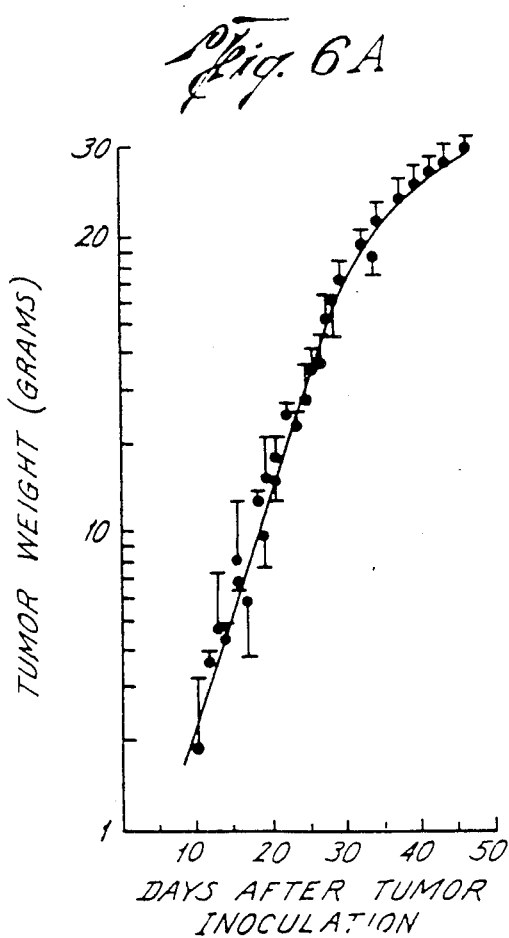
FIG. 6 (a) and (b). Graphs demonstrate the Gompertzian growth curve of the methylcholanthrene-induced sarcoma (MCA) and the Ward colon carcinoma (WCC) in the Fisher 344 rat. The MCA reaches its growth plateau at 60 grams while WCC reaches its plateau at 9 grams. The plateau phase of growth is related to the solid tumor outgrowing its blood supply and, hence, the reduced availability of $O_2$ and nutrients. There is no change in tumor growth when TPN is administered during the log phase of MCA growth. Host and MCA growth are significantly reduced when the host is fed a restricted diet. However, MCA growth becomes exponential when TPN is administered after 14 days of restricted diet.
Figure 6B:
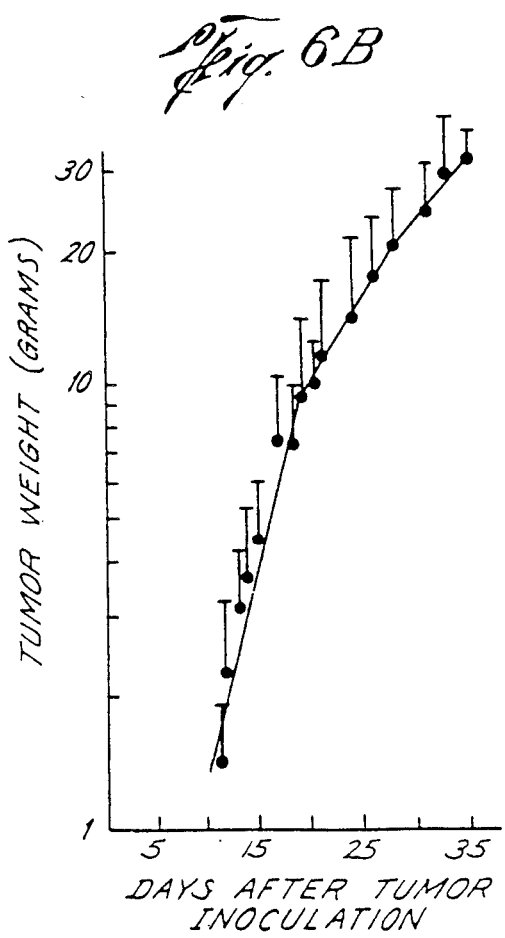

To test the above amino acid formula theory, Applicants conducted a preliminary study employing two different regimens, one a standard TPN solution, the other a control group. Each regimen was administered parenterally to adult rats for a period of 12 days. These rats had prior to treatment were implanted with transplantable colon tumor in the R flank. When the implant had grown to approximately 3 grams, the respective regimen was administered through a central venous catheter. As shown in FIG. 5, tumor growth in weight for the TPN group was significantly greater than the CHOW final tumor weight ($P<0.05$). a=$p<0.05$ compared with CHOW final tumor weight.

Figure 7:
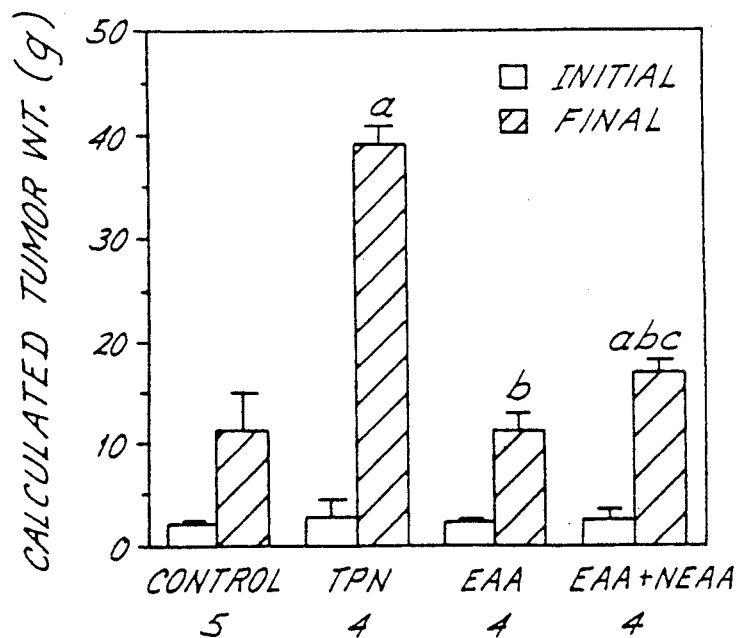
FIG. 7. Graph demonstrates the role of arginine in TPN (total parenteral nutrition) induced tumor growth observed in Example VIII. Fisher 344 rats with approximately 3 g transplantable colon tumors growing in the R flank were randomized to four groups and a central venous catheter was inserted. CONTROL received i.v. saline and oral chow ad libitum. The daily intake for these rats was $52\pm9$ cal and $584\pm104$ mg nitrogen. TPN consisted of 500 ml D50+500 ml 10% Travasol. The daily intake of TPN was $54\pm2$ cal and $550\pm15$ mg nitrogen. EAA describes a parenteral regimen consisting of 500 ml D50+500 ml 5.2% Aminess (essential amino acid only). The daily intake of EAA formula was $51\pm4$ cal and $270\pm10$ mg nitrogen. EAA +NEAA describes a parenteral regimen consisting of 500 ml D50+500 ml 5.2% Aminess with non-essential amino acids except arginine. The daily intake of EAA+-NEAA formula was $51\pm5$ cal and $574\pm15$ mg nitrogen. Hence, TPN and EAA±NEAA regimens were isonitrogenous and isocaloric with the only difference being the content of arginine. The parenteral regimens and saline were administered by continuous i.v. infusion for 12 days. This figure shows that TPN resulted in increased tumor growth compared with CONTROL. When EAA was given, no tumor growth was seen. When EAA+NEAA was given, there was a slight increase in tumor weight but much less than TPN.

The following studies, Examples VIII, IX, and X were designed to determine if the polyamine precursors in TPN solutions were responsible for stimulating tumor growth. In Example VIII, Fisher 344 male rats received an implant of Ward Colon carcinoma (WCC) in the R flank. When the implants had grown to approximately 3 grams, the rats were randomized to four groups, and a central venous catheter inserted. Four different regimens, including a standard TPN regimen, an EAA (essential amino acid) regimen, a EAA +NEAA (essential amino acids plus nonessential amino acids arginine free) and a Control group (i.v. saline and chow ad libitum), were infused for 12 days through the catheter. The content of each regimen is presented at Table VIII. As shown in FIG. 7, the greatest rate of tumor growth was exhibited in the TPN group. This study suggested arginine may be important in stimulating tumor growth.

Example IX was then devised to confirm the results in the previous study that suggested the presence of arginine in TPN solutions contributed to tumor growth. Fisher 344 male rats first received an implant of Ward Colon carcinoma. When the implant grew to approximately 4 grams, the animals were randomized into four groups and a central venous catheter inserted. Arginine and ornithine were then added back to separate TPN formulas. A third regimen wherein alanine was added back to the formulation was also used. A control group received saline intravenously (i.v.) and chow ad libitum. Each formulation was infused to a separate group of the above described rats. The contents of each of these regimens is outlined in Table IX. The respective solutions were parenterally administered for 6 days, after which time tumor growth was assessed. The results, as shown at FIG. 8, indicate that the addition of arginine increased WCC growth compared with control. (This is in contrast to the results obtained when either alanine or ornithine was added to the TPN solution, where there was observed no significant difference in tumor growth compared with control.)

Example X was then conducted to determine the concentration of arginine which increased tumor growth rate. Fisher 344 male rates were prepared as above and then randomized to four groups. Three arginine regimens with decreasing concentrations of arginine were formulated as outlined in Table X. A control group received saline o and chow ad libitum. After 12 days of parenteral administration of the various reqimens, tumor growth and urine amonia levels were assessed. The results, as shown in FIGS. 9 and 10, indicate that concentrations of arginine as low as 0.10% by weight were able to stimulate tumor growth rate over controls. Urine amonia levels were found to be inversely proportional to arginine regimen concentration, with the highest urine amonia levels present in the 0.10% arginine group. No detectable urine amonia was present in the urine of control group animals. These results suggest that arginine stimulates tumor growth rate and that a non-stimulatory concentration of arginine is most preferably less than 0.10% by weight final concentration.

These results indicate that cancer patients requiring TPN would benefit from a modified amino acid formula that deletes or reduces arginine. Additionally, a method of inhibiting tumor growth using formulations that contain I5 less than about 0.10% by weight arginine content is herein devised. Ornithine and/or citrulline should be added to these modified solutions in a concentration sufficient to maintain substrates for the urea cycle. Ornithine in at least a 0.5% by weight final concentration of the feeding formulation is adequate for urea cycle substrate purposes. The results obtained in the following experiments demonstrate that a specific amino acid formula with decreased arginine concentration (less than about 0.10% by weight) can effectively reduce tumor growth rate during nutritional therapy in a patient with malignant disease.

EXAMPLE VIII

This study was performed to demonstrate that the presence of particular precursors for polyamine biosynthesis in TPN solutions is responsible for stimulating tumor growth.

Male Fisher 344 rats were purchased from Timco Harlan-Spraque-Dawley (Houston, Texas). All rats were allowed a 7-day acclimation period with chow (Purina 5001) and water ad libitum. A Ward colon carcinoma (WCC) was implanted subcutaneously in the right flank of each animal under anesthesia. When these tumor implants had grown to approximately 3 grams, the rats were randomized to four groups and a central venous catheter inserted in the right flank. Each group of rats received one of the following 4 formulations: TPN; EAA (Essential Amino Acid Solution) with arginine; EAA+NEAA (Essential Amino Acid and Nonessential Amino Acid solution), without arginine; or Control (Saline). The control group of five rats received saline by infusion and rat chow. All solutions were administered for 12 days. In particular, the amino acid composition of the parenteral regimens used in this example is displayed in Table VIII. The TPN solution utilized in formulating a solution for one of the groups was Travesol 10%, whose amino acid composition is displayed in Table 1. Travesol 10% stock is used in compounding a feeding solution for general administration in patients with benign or malignant diseases.

Tumor weight was determined in each group before and after the 12-day treatment period. Results from this study are shown in FIG. 7. The Control group exhibited a tumor weight of 11±4 while the TPN treated group exhibited a tumor weight of 39±2g. There was no significant increase in tumor weight in the group receiving the EAA regimen (11+2). The EAA+NEAA arginine-free treated rats exhibited a slight increase in tumor weight, but much less than the TPN treated group (17 +4). The data indicates that TPN-stimulated tumor growth may be controlled by restricting arginine content.

ANIMAL POPULATION

Male Fisher 344 rats were purchased from Timco Harlan-Sprague-Dawley (Houston, Texas). All rats were allowed a 7-day acclimation period with chow (Purina 5001) and water ad libitum. Each rat was then inoculated subcutaneously in the right flank with a transplantable Ward Colon carcinoma (WCC). When the implants grew to approximately 3 grams in weight, the rats were randomized to four groups.

NUTRITIONAL REGIMEN

The content of the solutions used in this study appear at Table VIII. TPN solutions consisted of 500 ml D50W+500 ml 10% Travesol. EAA regimen consisted of 500 ml D50W +500 ml essential amino acid (EAA) solution. EAA +NEAA consisted of 500 ml D50W+500 ml essential and non-essential amino acids (NEAA) deleting arginine. Control received intravenous saline and chow ad libitum. All solutions were administered through a central venous catheter by continuous i.v. infusion for 12 days. Daily intake of control rats was 52±9 cal and 584+104 mg nitrogen. Daily intake of TPN was 54±2 cal and 550±15 mg nitrogen. EAA daily intake was 51+4 cal and 270±10 mg nitrogen. EAA+NEAA regimen daily intake was 51±5 cal and 574±15 mg nitrogen. TPN and EAA+NEAA regimens were isonitrogenous and isocaloric with the only difference being the content of arginine.

STUDY DESIGN

Each of 18 Fisher adult male rats were given a subcutaneous implantation (in the right flank) of a fixed volume of tumorous cells. When the implant of tumorous Ward colon carcinoma cells reached about a 3 gram weight, the rats were randomized to four groups and a central venous catheter inserted. Each group was to receive either TPN, EAA formula, EAA+NEAA (arginine free) or Saline (control group) for a period of 12 days. Calculations of each tumor weight in grams in each of the animals was made after the 12 day regimen. In this manner, each rat served as its own control in determining the effect of the particular regimen on tumor growth. Analysis of data was done by a student's t-test, comparing tumor growth before and after the designated regimen between treatment groups.

TUMOR GROWTH DETERMINATIONS

The TPN-induced tumor growth was determined from the calculated tumor weight in grams after the 12-day treatment. The results are shown in FIG. 7. Tumor growth was assessed by two-dimensional measurements with calipers, (length and width) and the equation, length (cm) ×(width [cm]$^2 \times \frac{1}{2}$=grams of tumor tissue, was used to estimate tumor weight.

The results are demonstrated in FIG. 7. As FIG. 7 indicates, TPN resulted in tumor growth stimulation compared with Control. EAA did not stimulate tumor growth compared with Control. There was a slight increase in tumor growth with EAA+NEAA compared with Control, but tumor size was markedly lower than TPN tumors. The EAA+ NEAA regimens did not contain arginine, thus, it is deduced that the presence of arginine in TPN solutions is important in stimulating tumor growth. TPN solutions contain final arginine concentrations of about 1% by weight in the feeding formulations.

TABLE VIII

Amino Acid Composition of Parenteral Regimens of Rats

| Amino Acid | % N | Concentrations of each amino acid(mg) per 100 ml | | |
|---|---|---|---|---|
| | | EAA | EAA + NEAA | TPN |
| LEUCINE | 10.67 | 825 | 825 | 730 |
| METHIONINE | 9.39 | 825 | 825 | 400 |
| PHENYLALANINE | 8.48 | 825 | 825 | 560 |
| LYSINE | 19.16 | 600 | 600 | 580 |
| VALINE | 11.96 | 600 | 600 | 580 |
| ISOLEUCINE | 10.68 | 525 | 525 | 600 |
| THREONINE | 11.76 | 375 | 375 | 420 |
| TRYPTOPHAN | 13.72 | 188 | 188 | 180 |
| HISTIDINE | 27.08 | 412 | 412 | 480 |
| ALANINE | 15.72 | — | 3210 | 2070 |
| ARGININE | 32.16 | — | — | 1150 |
| GLYCINE | 18.66 | — | 1599 | 1030 |
| PROLINE | 12.17 | — | 1059 | 680 |
| SERINE | 13.33 | — | 780 | 500 |
| TYROSINE | 7.73 | — | 51 | 40 |

The EAA regimen was formulated with 500 ml of Aminess$^R$, 500 ml D50W, electrolytes, and multivitamins. EAA + NEAA regimen was formulated with 500 ml of 10% EAA + NEAA, 500 ml D50W, electrolytes, and multivitamins. TPN regimen consisted of 500 ml 10% Travasol, 500 ml D50W, electrolytes, and multivitamins. These were administered by continuous infusion through a central venous catheter, the flow rate being controlled with Holter 903 pump. The amino acid concentration(mg/ 100 ml) in this table is the concentration of the 500 ml amino acid solution before formulation. Formulation was accomplished by the addition of a glucose solution to the above described stock.

EXAMPLE IX

This study was performed to determine whether the addition of arginine and ornithine to a total parenteral nutritional (TPN) regimen would stimulate tumor growth. TPN regimens containing alanine, arginine or ornithine were administered i.v. A control group received saline and chow ad libitum. The various regimens were administered parenterally to male Fisher 344 rats with Ward Colon Carcinoma implants that had grown to approximately 4 grams. Each group consisted of 5 rats. Tumor size was determined before and after the designated regimen for each animal. Percent increase in tumor weights in the ALANINE regimen group and the ORNITHINE regimen group did not differ from the CONTROL group. An increase in percent tumor growth compared with Control was observed in the ARGININE group, yet no significant difference was observed in the ALANINE group. The data indicates that cancer patients requiring TPN would benefit from a modified amino acid formula that deletes or reduces arginine content.

ANIMAL POPULATION

Male Fisher 344 rats were purchased from Timco Harlan-Sprague-Dawley (Houston, Texas). All rats were allowed a 7-day acclimation period with chow (Purina 5001) and water ad libitum. A Ward Colon Carcinoma (WCC) was implanted subcutaneously in the right flank of each rat under anesthesia. When the implant grew to approximately 3 grams, the rats were randomized to four groups. A central venous catheter was then inserted into each rat.

NUTRITIONAL REGIMEN

Four nutritional regimens were formulated for this study. Each group of rats were given one of these regimens.

The amino acid composition of each regimen is displayed at Table IX. The ALANINE regimen consisted of 500 ml D50W+250 ml 5.5% essential amino acid (EAA, Nephramine)+294 mg/100ml alanine. ARGININE regimen consisted of 500 ml D50W+250 ml 5.5% EAA+575mg/100ml arginine. ORNITHINE regimen consisted of 500ml D50W+250ml 5.5% EAA+436 mg/100 ml ornithine. The CONTROL regimen consisted of saline infusion with chow supplied ad libitum. Table IX defines the composition of each of these formulations. The solutions were infused for 6 days and tumor growth was assessed.

STUDY DESIGN

Each of 20 Fisher adult male rats were given a subcutaneous implantation in the right flank of a fixed volume of tumorous cells, Wards colon carcinoma. When the implant grew to approximately 3 grams, the rats were randomized into 4 different treatment groups. A central venous catheter was then inserted. Each group was to receive a regimen of ALANINE, ORNITHINE, ARGININE, or SALINE (CONTROL) and chow ad libitum for 6 days. Tumor growth in each animal was assessed for percent increase in tumor weight compared to that animals pre-regimen tumor weight. In this manner, each rat served as his or her own control in determining the effect of the particular regimen on tumor growth. The various treatment regimens were also compared as against the CONTROL group for percent tumor growth.

PERCENT TUMOR GROWTH DETERMINATIONS

Tumor growth was assessed by a measure of percent increase in tumor weight before and after the designated regimen. The results are demonstrated in FIG. 9. As demonstrated in FIG. 8, the ALANINE formula did not stimulate WCC tumor growth compared with CONTROL. Increased WCC tumor growth compared with CONTROL was observed when ARGININE was substituted for alanine at an equimolar amount. There was no significant difference in tumor growth compared with CONTROL when TPN formula contained ORNITHINE.

TABLE IX

Amino acid composition of parenteral regimens of rats

| Amino Acid | Concentration of each amino acid(mg) per 100 ml | | |
|---|---|---|---|
| | ALANINE | ARGININE | ORNITHINE |
| LEUCINE | 293 | 293 | 293 |
| METHIONINE | 293 | 293 | 293 |
| PHENYLALAN-INE | 293 | 293 | 293 |
| LYSINE | 213 | 213 | 213 |
| VALINE | 213 | 213 | 213 |
| ISOLEUCINE | 187 | 187 | 187 |
| THREONINE | 110 | 110 | 110 |
| TRYPTOPHAN | 55 | 55 | 55 |
| HISTIDINE | 143 | 143 | 143 |
| ALANINE | 294 | 0 | 0 |
| ARGININE | 0 | 575 | 0 |
| ORNITHINE | 0 | 0 | 436 |

The final regimens were formulated with 250 ml of the above amino acid solution, 500 ml D50W, TPN-electrolytes (Abbott Laboratories), and multivitamins. These were administered by continuous infusion through a central venous catheter, the flow rate being controlled with Holter 903 pump. Concentration of amino acid represents final concentration in total volume of 750 ml. Alanine, arginine, and ornithine were added in equimolar amounts.

EXAMPLE X

This study was performed to determine the concentrations of arginine which stimulate tumor growth. Modified TPN solutions containing 0.10%, 0.25% or 0.65% Arginine by weight final feeding formulation concentrations were administered i.v. A control group received i.v. 0.90% NaCl (saline) and chow ad libitum. The various regimens were administered parenterally to male Fisher 344 rats with Ward Colon Carcinoma implants that had grown to approximately 4 grams. Each of the Arginine groups consisted of 4 rats while the control group consisted of 3 rats. Tumor size was determined before and after the designated regimen for each animal. Urine ammonia levels were also determined before and after the designated regimen for each animal. The post-treatment tumor weights (g) in the 0.10%, 0.25% and 0.65% Arginine groups did differ significantly from the Control group. However, no significant difference was observed in post-treatment tumor weights between the various Arginine groups. The data indicates that patients requiring TPN would benefit from a modified amino acid formula that deletes or reduces arginine content to less than 0.10% by weight final concentration.

ANIMAL POPULATION

Male Fisher 344 rats were purchased from Timco Harlan-Sprague-Dawley (Houston, Texas). All rats were allowed a 7-day acclimation period with chow (Purina 500) and water ad libitum. A Ward Colon Carcinoma (WCC) was implanted subcutaneously in the right flank of 15 rats under anesthesia. When the implant grew to approximately 4 grams, the rats were randomized to 3 groups of 4 rats each and 1 group of 3 rats. A central venous catheter Was then inserted into each rat.

NUTRITIONAL REGIMEN

Four nutritional regimens were formulated for this study. Each group of rats was given one of these regimens.

The amino acid composition of each regimen is displayed at Table X. The 0.65% arginine regimen consisted of 500 ml D50W+500 ml Aminess ®+0.65 g./100 ml. arginine. The 0.25% arginine regimen consisted of 500 15 ml D50W+500 ml Aminess ®+0.25 g./100 ml arginine. The 0.10% arginine regimen consisted of 500 ml D 50W+500 ml Aminess ®+0.10 g./100 ml arginine. The CONTROL regimen consisted of saline infusion with chow ad libitum. Table X also defines the mixture and proportion of other amino acids contained in each of the three arginine regimens. The solutions were infused for 12 days. Tumor growth and urine ammonia levels were then assessed and compared to pre-treatment levels.

STUDY DESIGN

Each of 15 Fisher adult male rats were given a subcutaneous implantation in the right flank of a fixed volume of tumorous cells, Wards Colon Carcinoma. When the implant grew to approximately 4 grams, the rats were randomized into 4 treatment groups. A central venous catheter was then inserted. Each group was to receive a regimen of 0.10%, 0.25% or 0.65% arginine or saline (control) and chow ad libitum for 12 days. Tumor growth in each arginine regimen animal was assessed for weight increase compared to tumor growth exhibited in the saline (control) regimen animals. Also, tumor growth in each animal was assessed for increase in tumor weight compared to that animals pre-regimen tumor weight. In this manner, each rat served as his or her own control in determining the effect of the particular regimen on tumor growth. Urine ammonia levels were also determined for each of the arginine regimen animals. These values were compared to the urine ammonia levels of saline (control) regimen animals.

TUMOR GROWTH DETERMINATIONS

Tumor growth was assessed by a measure of increase in tumor weight before and after the designated regimen as described in Example VIII. The results are demonstrated in FIG. 9. As demonstrated in FIG. 9, post-treatment tumor weights in the 0.10%, 0.25% and 0.65% arginine concentration regimens did not vary significantly among groups. However, all 3 arginine regimen groups did exhibit post-treatment tumor weights significantly greater than the saline (control) regimen group tumor weights.

URINE AMMONIA DETERMINATIONS

Urine ammonia levels were assessed as a function of urine NH4 (mg./24 hours) in each animal post-treatment. The levels obtained from animals of each arginine treatment group were averaged and compared to the average level obtained in the saline (control) treated group. As demonstrated in FIG. 10, there was an inverse relationship between the concentration of arginine given in the regimen to the level of urine ammonia. Thus, the 0.25% arginine group exhibited higher urine ammonia levels compared to the 0.65% arginine group, and the 0.10% arginine group exhibited higher urine ammonia levels compared to the 0.25% arginine group. All arginine groups (0.10%, 0.25%, 0.65%) displayed urine ammonia levels significantly higher than the saline (control) treated group.

TABLE X

Amino acid composition of parenteral regimens of rats

| Amino Acid | Concentration of each amino acid (mg) per 100 ml | | |
|---|---|---|---|
| | 0.1% arg | 0.25% arg | 0.65% |
| Essential | | | |
| LEUCINE | 413 | 413 | 413 |
| METHIONINE | 413 | 413 | 413 |
| PHENYLALANINE | 413 | 413 | 413 |
| LYSINE | 300 | 300 | 300 |
| VALINE | 300 | 300 | 300 |
| ISOLEUCINE | 263 | 263 | 263 |
| THREONINE | 188 | 188 | 188 |
| TRYPTOPHAN | 94 | 94 | 94 |
| HISTIDINE | 206 | 206 | 206 |
| Nonessential | | | |
| ALANINE | 1035 | 1035 | 1035 |
| ARGININE | 100 | 250 | 650 |
| GLYCINE | 1463 | 1203 | 515 |
| PROLINE | 340 | 340 | 340 |
| SERINE | 250 | 250 | 250 |

The TPN regimen was formulated with 500 ml of Aminess ®, 500 ml D50W, electrlytes, and multivitamins. The amino acids, alanine, arginine, glycine, proline and serine were added to the TPN regimen. These solutions were administered by continuous infusion through a central venous catheter, the flow rate being controlled with Holter 903 pump. The amino acid concentration (mg/100 ml) in this table is the concentration of the amino acids in the one liter TPN solution. Control received i.v. 0.90% NaCl(saline) and chow ad libitum. The 0.10% arg group received a TPN formula with a final arginine concentration of 0.1 g/100 ml. The 0.25% arg group received a TPN formula with a final concentration of 0.25 g/100 ml. The 0.65% arg group received a TPN formula with a final arginine concentration of 0.65 g/100 ml.

Those of skill in the art will recognize that, although the present invention is disclosed in terms of specific embodiments, one may depart from such embodiments and still remain within the scope of the invention. All such departures are considered to be within the scope of pending claims.

What is claimed is:

1. A formulation for the prevention of stimulation of tumor growth in patients with malignant disease, comprising a pharmacologically acceptable amount of:
   (a) a mixture of the following essential amino acids in a concentration of between 0.01 to 5.0% by weight of the formulation:
   leucine;
   methionine;
   phenylalanine;
   lysine;
   valine;
   isoleucine;
   threonine;
   tryptophan;
   histidine;
   (b) at least one amino acid selected from the group consisting of:
   0.01-2% by weight final concentration of citrulline; and
   0.51%-5% by weight final concentration of ornithine;
   (c) at least one non-essential amino acid in a concentration of between 0.01-5% by weight of the formulation selected from the group consisting of:
   alanine;
   proline;
   serine; and
   tyrosine; and
   (d) less than 0.10% by weight final concentration of arginine, the foregoing amino acids being dispersed in a suitable liquid medium.

2. The formulation of claim 1 wherein the formulation is essentially arginine-free.

3. The formulation of claim 1 wherein the selected non-essential amino acid is alanine.

4. The formulation of claim 3 wherein the concentration of alanine is in the weight range of between 300 to 3,500 mg. for every 100 milliliters of the formulation.

5. The formulation of claim 1 wherein the selected group (b) amino acids are citrulline and ornithine.

6. The formulation of claim 5 wherein citrulline and ornithine are present in the following ranges of concentration by weight in the final feeding formulation:
   0.01-2.0% citrulline;
   0.01-0.5% ornithine.

7. The formulation of claim 1 wherein the selected group (b) amino acid is citrulline.

8. The formulation of claim 1 wherein the selected group (b) amino acid is ornithine in a final concentration of greater than about 0.5% by weight of the feeding formulation.

9. The formulation of claim 1 wherein the concentration of the selected group (b) amino acid is greater than about 0.50% by weight final concentration of the feeding formulation.

10. The formulation of claim 1 wherein the concentration of arginine is less than about 0.10% by weight final concentration of the feeding formulation.

11. The formulation of claim 1 wherein the concentration of ornithine is greater than about 0.50% by weight final concentration of the feeding formulation.

12. The formulation of claim 1 wherein the concentration of citrulline is in the range of 0.01 to 2% by weight final concentration of the feeding formulation.

13. The formulation of claim 1 wherein the pharmacologically acceptable amount of essential amino acids comprises between about 0.01 and about 5.0 grams of each essential amino acid for every 100 milliliters of the feeding formulation.

14. The formulation of claim 1 wherein the pharmacologically acceptable amount of the selected non-essential amino acids comprise the following weight range of the amino acid for ever 100 milliliters of the formulation:
   200 to 3500 mg of alanine
   250 to 2500 mg of glycine
   100 to 1500 mg of proline
   5 to 650 mg of serine
   30 to 60 mg of tyrosine.

15. The formulation of claim 1 wherein the pharmacologically acceptable amount of essential amino acids comprise the following weight range of the amino acid for every 100 milliliters of the formulation:
   250 to 1400 mg of leucine
   200 to 1400 mg of isoleucine
   200 to 1250 mg of valine
   100 to 900 mg of phenylalanine
   50 to 850 mg of methionine
   150 to 750 mg of lysine
   85 to 500 mg of histidine
   100 to 500 mg of threonine
   50 to 200 mg of tryptophan.

16. The formulation of claim 1 wherein the suitable liquid medium is a glucose solution.

17. A method for inhibiting tumor growth in an animal with malignant disease by administering to said animal the formulations defined in any one of claim 1, 2-8, or 9-16.

18. The method as claim 17 wherein the animal is a human.

19. The method of claim 17 wherein administration of the formulation is parenteral.

* * * * *